US011504625B2

(12) United States Patent
Stevens

(10) Patent No.: US 11,504,625 B2
(45) Date of Patent: Nov. 22, 2022

(54) COLOR BLINDNESS DIAGNOSTIC SYSTEM

(71) Applicant: Electronic Arts Inc., Redwood City, CA (US)

(72) Inventor: Karen Elaine Stevens, Maitland, FL (US)

(73) Assignee: ELECTRONIC ARTS INC., Redwood City, CA (US)

(*) Notice: Subject to any disclaimer, the term of this patent is extended or adjusted under 35 U.S.C. 154(b) by 178 days.

(21) Appl. No.: 16/792,030

(22) Filed: Feb. 14, 2020

(65) Prior Publication Data

US 2021/0252403 A1    Aug. 19, 2021

(51) Int. Cl.
| | | |
|---|---|---|
| G06F 3/048 | (2013.01) | |
| A63F 13/67 | (2014.01) | |
| G06T 11/00 | (2006.01) | |
| A63F 13/77 | (2014.01) | |
| A63F 13/533 | (2014.01) | |
| A61B 3/06 | (2006.01) | |
| G06F 3/0481 | (2022.01) | |

(52) U.S. Cl.
CPC ............ *A63F 13/67* (2014.09); *A61B 3/066* (2013.01); *A63F 13/533* (2014.09); *A63F 13/77* (2014.09); *G06F 3/0481* (2013.01); *G06T 11/001* (2013.01); *A61B 2503/12* (2013.01); *A63F 2300/308* (2013.01); *A63F 2300/6027* (2013.01); *G06T 2200/24* (2013.01)

(58) Field of Classification Search
None
See application file for complete search history.

(56) References Cited

U.S. PATENT DOCUMENTS

| | | | |
|---|---|---|---|
| 5,274,801 A | 12/1993 | Gordon | |
| 5,548,798 A | 8/1996 | King | |
| 5,982,389 A | 11/1999 | Guenter et al. | |
| 5,999,195 A | 12/1999 | Santangeli | |
| 6,064,808 A | 5/2000 | Kapur et al. | |
| 6,088,040 A | 7/2000 | Oda et al. | |
| 6,253,193 B1 | 6/2001 | Ginter et al. | |
| 6,556,196 B1 | 4/2003 | Blanz et al. | |
| 6,961,060 B1 | 11/2005 | Mochizuki et al. | |

(Continued)

FOREIGN PATENT DOCUMENTS

| | | |
|---|---|---|
| CN | 102509272 A | 6/2012 |
| CN | 103546736 A | 1/2014 |

(Continued)

OTHER PUBLICATIONS

Habibie et al., "A Recurrent Variational Autoencoder for Human Motion Synthesis", 2017, in 12 pages.

(Continued)

*Primary Examiner* — Thanh T Vu
(74) *Attorney, Agent, or Firm* — Knobbe, Martens, Olson & Bear, LLP

(57) ABSTRACT

Systems and methods for determining whether to enable color blind accessibility settings within the course of a user interactive narrative are described herein. Virtual color blindness indication objects containing colors that are visibly distinguishable within a single dichromatic visual spectrum can be utilized in objectives to determine a user's dichromatic visual deficiency type.

18 Claims, 10 Drawing Sheets
(6 of 10 Drawing Sheet(s) Filed in Color)

Color Blind Target Set Generation

(56) References Cited

U.S. PATENT DOCUMENTS

| | | |
|---|---|---|
| 7,006,090 B2 | 2/2006 | Mittring |
| 7,403,202 B1 | 7/2008 | Nash |
| 7,415,152 B2 | 8/2008 | Jiang et al. |
| 7,944,449 B2 | 5/2011 | Petrovic et al. |
| 8,100,770 B2 | 1/2012 | Yamazaki et al. |
| 8,142,282 B2 | 3/2012 | Canessa et al. |
| 8,154,544 B1 | 4/2012 | Cameron et al. |
| 8,207,971 B1 | 6/2012 | Koperwas et al. |
| 8,267,764 B1 | 9/2012 | Aoki et al. |
| 8,281,281 B1 | 10/2012 | Smyrl et al. |
| 8,395,626 B2 | 3/2013 | Millman |
| 8,398,476 B1 | 3/2013 | Sidhu et al. |
| 8,406,528 B1 | 3/2013 | Hatwich |
| 8,540,560 B2 | 9/2013 | Crowley et al. |
| 8,599,206 B2 | 12/2013 | Hodgins et al. |
| 8,624,904 B1 | 1/2014 | Koperwas et al. |
| 8,648,863 B1 | 2/2014 | Anderson et al. |
| 8,860,732 B2 | 10/2014 | Popovic et al. |
| 8,914,251 B2 | 12/2014 | Ohta |
| 9,117,134 B1 | 8/2015 | Geiss et al. |
| 9,256,973 B2 | 2/2016 | Koperwas et al. |
| 9,317,954 B2 | 4/2016 | Li et al. |
| 9,483,860 B2 | 11/2016 | Hwang et al. |
| 9,616,329 B2 | 4/2017 | Szufnara et al. |
| 9,741,146 B1 | 8/2017 | Nishimura |
| 9,811,716 B2 | 11/2017 | Kim et al. |
| 9,826,898 B1 | 11/2017 | Jin et al. |
| 9,827,496 B1 | 11/2017 | Zinno |
| 9,858,700 B2 | 1/2018 | Rose et al. |
| 9,947,123 B1 | 4/2018 | Green |
| 9,984,658 B2 | 5/2018 | Bonnier et al. |
| 9,990,754 B1 | 6/2018 | Waterson et al. |
| 10,022,628 B1 | 7/2018 | Matsumiya et al. |
| 10,096,133 B1 | 10/2018 | Andreev |
| 10,118,097 B2 | 11/2018 | Stevens |
| 10,198,845 B1 | 2/2019 | Bhat et al. |
| 10,314,477 B1 | 6/2019 | Goodsitt et al. |
| 10,388,053 B1 | 8/2019 | Carter, Jr. et al. |
| 10,403,018 B1 | 9/2019 | Worsham |
| 10,535,174 B1 | 1/2020 | Rigiroli et al. |
| 10,726,611 B1 | 7/2020 | Court |
| 10,733,765 B2 | 8/2020 | Andreev |
| 10,755,466 B2 | 8/2020 | Chamdani et al. |
| 10,792,566 B1 | 10/2020 | Schmid |
| 10,856,733 B2 | 12/2020 | Anderson et al. |
| 10,860,838 B1 | 12/2020 | Elahie et al. |
| 10,878,540 B1 | 12/2020 | Stevens |
| 10,902,618 B2 | 1/2021 | Payne et al. |
| 11,113,860 B2 | 9/2021 | Rigiroli et al. |
| 11,217,003 B2 | 1/2022 | Akhoundi et al. |
| 11,232,621 B2 | 1/2022 | Akhoundi et al. |
| 11,295,479 B2 | 4/2022 | Andreev |
| 2002/0054054 A1 | 5/2002 | Sanbe |
| 2002/0089504 A1 | 7/2002 | Merrick et al. |
| 2002/0180739 A1 | 12/2002 | Reynolds et al. |
| 2003/0038818 A1 | 2/2003 | Tidwell |
| 2004/0027352 A1 | 2/2004 | Minakuchi |
| 2004/0227760 A1 | 11/2004 | Anderson et al. |
| 2004/0227761 A1 | 11/2004 | Anderson et al. |
| 2005/0237550 A1 | 10/2005 | Hu |
| 2006/0036514 A1 | 2/2006 | Steelberg et al. |
| 2006/0149516 A1 | 7/2006 | Bond et al. |
| 2006/0217945 A1 | 9/2006 | Leprevost |
| 2006/0262114 A1 | 11/2006 | Leprevost |
| 2007/0085851 A1 | 4/2007 | Muller et al. |
| 2007/0097125 A1 | 5/2007 | Xie et al. |
| 2008/0049015 A1 | 2/2008 | Elmieh et al. |
| 2008/0111831 A1 | 5/2008 | Son et al. |
| 2008/0152218 A1 | 6/2008 | Okada |
| 2008/0268961 A1 | 10/2008 | Brook |
| 2008/0316202 A1 | 12/2008 | Zhou et al. |
| 2009/0066700 A1 | 3/2009 | Harding et al. |
| 2009/0315839 A1 | 12/2009 | Wilson et al. |
| 2010/0134501 A1 | 6/2010 | Lowe et al. |
| 2010/0251185 A1 | 9/2010 | Pattenden |
| 2010/0277497 A1 | 11/2010 | Dong et al. |
| 2011/0012903 A1 | 1/2011 | Girard |
| 2011/0074807 A1 | 3/2011 | Inada et al. |
| 2011/0086702 A1 | 4/2011 | Borst et al. |
| 2011/0119332 A1 | 5/2011 | Marshall et al. |
| 2011/0128292 A1 | 6/2011 | Ghyme et al. |
| 2011/0164831 A1 | 7/2011 | Van Reeth et al. |
| 2011/0187731 A1 | 8/2011 | Tsuchida |
| 2011/0269540 A1 | 11/2011 | Gillo et al. |
| 2011/0292055 A1 | 12/2011 | Hodgins et al. |
| 2012/0083330 A1 | 4/2012 | Ocko |
| 2012/0115580 A1 | 5/2012 | Hornik et al. |
| 2012/0220376 A1 | 8/2012 | Takayama et al. |
| 2012/0244941 A1 | 9/2012 | Ostergren et al. |
| 2012/0303343 A1 | 11/2012 | Sugiyama et al. |
| 2012/0313931 A1 | 12/2012 | Matsuike et al. |
| 2013/0050464 A1 | 2/2013 | Kang |
| 2013/0063555 A1 | 3/2013 | Matsumoto et al. |
| 2013/0120439 A1 | 5/2013 | Harris et al. |
| 2013/0121618 A1 | 5/2013 | Yadav |
| 2013/0222433 A1 | 8/2013 | Chapman et al. |
| 2013/0235045 A1 | 9/2013 | Corazza et al. |
| 2013/0263027 A1 | 10/2013 | Petschnigg et al. |
| 2013/0311885 A1 | 11/2013 | Wang et al. |
| 2014/0002463 A1 | 1/2014 | Kautzman et al. |
| 2014/0066196 A1* | 3/2014 | Crenshaw ............... A63F 13/52 463/31 |
| 2014/0198106 A1 | 7/2014 | Sumner et al. |
| 2014/0198107 A1 | 7/2014 | Thomaszewski et al. |
| 2014/0327694 A1 | 11/2014 | Cao et al. |
| 2014/0340644 A1* | 11/2014 | Haine ..................... A61B 3/066 351/239 |
| 2015/0113370 A1 | 4/2015 | Flider |
| 2015/0126277 A1 | 5/2015 | Aoyagi |
| 2015/0187113 A1 | 7/2015 | Rubin et al. |
| 2015/0235351 A1 | 8/2015 | Mirbach et al. |
| 2015/0243326 A1 | 8/2015 | Pacurariu et al. |
| 2015/0381925 A1 | 12/2015 | Varanasi et al. |
| 2016/0026926 A1 | 1/2016 | Yeung et al. |
| 2016/0042548 A1 | 2/2016 | Du et al. |
| 2016/0071470 A1 | 3/2016 | Kim et al. |
| 2016/0217723 A1 | 7/2016 | Kim et al. |
| 2016/0307369 A1 | 10/2016 | Freedman et al. |
| 2016/0314617 A1 | 10/2016 | Forster et al. |
| 2016/0354693 A1 | 12/2016 | Yan et al. |
| 2017/0132827 A1 | 5/2017 | Tena et al. |
| 2017/0301310 A1* | 10/2017 | Bonnier ................. G09G 5/026 |
| 2017/0301316 A1 | 10/2017 | Farell |
| 2018/0024635 A1 | 1/2018 | Kaifosh et al. |
| 2018/0122125 A1 | 5/2018 | Brewster |
| 2018/0165864 A1 | 6/2018 | Jin et al. |
| 2018/0211102 A1 | 7/2018 | Alsmadi |
| 2018/0239526 A1 | 8/2018 | Varanasi et al. |
| 2019/0139264 A1 | 5/2019 | Andreev |
| 2019/0392587 A1 | 12/2019 | Nowozin et al. |
| 2020/0294299 A1 | 9/2020 | Rigiroli et al. |
| 2020/0310541 A1 | 10/2020 | Reisman et al. |
| 2020/0364303 A1 | 11/2020 | Liu et al. |
| 2021/0019916 A1 | 1/2021 | Andreev |
| 2021/0217184 A1 | 7/2021 | Payne et al. |
| 2021/0308580 A1 | 10/2021 | Akhoundi et al. |
| 2021/0312688 A1 | 10/2021 | Akhoundi et al. |
| 2021/0312689 A1 | 10/2021 | Akhoundi et al. |
| 2022/0198733 A1 | 6/2022 | Akhoundi et al. |

FOREIGN PATENT DOCUMENTS

| | | |
|---|---|---|
| CN | 105405380 A | 3/2016 |
| CN | 105825778 A | 8/2016 |
| JP | 2018-520820 A | 8/2018 |
| JP | 2019-162400 A | 9/2019 |

OTHER PUBLICATIONS

Anagnostopoulos et al., "Intelligent modification for the daltonization process", International Conference on Computer Vision Published in 2007 by Applied Computer Science Group of digitized paintings.

(56) References Cited

OTHER PUBLICATIONS

Andersson, S., Goransson, J.: Virtual Texturing with WebGL. Master's thesis, Chalmers University of Technology, Gothenburg, Sweden (2012).
Avenali, Adam, "Color Vision Deficiency and Video Games", The Savannah College of Art and Design, Mar. 2013.
Badlani et al., "A Novel Technique for Modification of Images for Deuteranopic Viewers", May 2016.
Belytschko et al., "Assumed strain stabilization of the eight node hexahedral element," Computer Methods in Applied Mechanics and Engineering, vol. 105(2), pp. 225-260 (1993), 36 pages.
Belytschko et al., Nonlinear Finite Elements for Continua and Structures, Second Edition, Wiley (Jan. 2014), 727 pages (uploaded in 3 parts).
Blanz V, Vetter T. A morphable model for the synthesis of 3D faces. In Proceedings of the 26th annual conference on Computer graphics and interactive techniques Jul. 1, 1999 (pp. 187-194). ACM Press/Addison-Wesley Publishing Co.
Blanz et al., "Reanimating Faces in Images and Video" Sep. 2003, vol. 22, No. 3, pp. 641-650, 10 pages.
Chao et al., "A Simple Geometric Model for Elastic Deformations", 2010, 6 pgs.
Cook et al., Concepts and Applications of Finite Element Analysis, 1989, Sections 6-11 through 6-14.
Cournoyer et al., "Massive Crowd on Assassin's Creed Unity: AI Recycling," Mar. 2, 2015, 55 pages.
Dick et al., "A Hexahedral Multigrid Approach for Simulating Cuts in Deformable Objects", IEEE Transactions on Visualization and Computer Graphics, vol. X, No. X, Jul. 2010, 16 pgs.
Diziol et al., "Robust Real-Time Deformation of Incompressible Surface Meshes", to appear in Proceedings of the 2011 ACM SIGGRAPH/Eurographics Symposium on Computer Animation (2011), 10 pgs.
Dudash, Bryan. "Skinned instancing." NVidia white paper(2007).
Fikkan, Eirik. Incremental loading of terrain textures. MS thesis. Institutt for datateknikk og informasjonsvitenskap, 2013.
Geijtenbeek, T. et al., "Interactive Character Animation using Simulated Physics", Games and Virtual Worlds, Utrecht University, The Netherlands, The Eurographics Association 2011, 23 pgs.
Georgii et al., "Corotated Finite Elements Made Fast and Stable", Workshop in Virtual Reality Interaction and Physical Simulation VRIPHYS (2008), 9 pgs.
Halder et al., "Image Color Transformation for Deuteranopia Patients using Daltonization", IOSR Journal of VLSI and Signal Processing (IOSR-JVSP) vol. 5, Issue 5, Ver. I (Sep.-Oct. 2015), pp. 15-20.
Han et al., "On-line Real-time Physics-based Predictive Motion Control with Balance Recovery," Eurographics, vol. 33(2), 2014, 10 pages.
Hernandez, Benjamin, et al. "Simulating and visualizing real-time crowds on GPU clusters." Computación y Sistemas 18.4 (2014): 651-664.
Hu G, Chan CH, Yan F, Christmas W, Kittier J. Robust face recognition by an albedo based 3D morphable model. In Biometrics (IJCB), 2014 IEEE International Joint Conference on Sep. 29, 2014 (pp. 1-8). IEEE.
Hu Gousheng, Face Analysis using 3D Morphable Models, Ph.D. Thesis, University of Surrey, Apr. 2015, pp. 1-112.
Irving et al., "Invertible Finite Elements for Robust Simulation of Large Deformation", Eurographics/ACM SIGGRAPH Symposium on Computer Animation (2004), 11 pgs.
Kaufmann et al., "Flexible Simulation of Deformable Models Using Discontinuous Galerkin FEM", Oct. 1, 2008, 20 pgs.
Kavan et al., "Skinning with Dual Quaternions", 2007, 8 pgs.
Kim et al., "Long Range Attachments—A Method to Simulate Inextensible Clothing in Computer Games", Eurographics/ACM SIGGRAPH Symposium on Computer Animation (2012), 6 pgs.
Klein, Joseph. Rendering Textures up Close in a 3D Environment Using Adaptive Micro-Texturing. Diss. Mills College, 2012.
Komura et al., "Animating reactive motion using momentum-based inverse kinematics," Computer Animation and Virtual Worlds, vol. 16, pp. 213-223, 2005, 11 pages.
Lee, Y. et al., "Motion Fields for Interactive Character Animation", University of Washington, Bungie, Adobe Systems, 8 pgs, obtained Mar. 20, 2015.
Levine, S. et al., "Continuous Character Control with Low-Dimensional Embeddings", Stanford University, University of Washington, 10 pgs, obtained Mar. 20, 2015.
Macklin et al., "Position Based Fluids", to appear in ACM TOG 32(4), 2013, 5 pgs.
McAdams et al., "Efficient Elasticity for Character Skinning with Contact and Collisions", 2011, 11 pgs.
McDonnell, Rachel, et al. "Clone attack! perception of crowd variety." ACM Transactions on Graphics (TOG). vol. 27. No. 3. ACM, 2008.
Muller et al., "Meshless Deformations Based on Shape Matching", SIGGRAPH 2005, 29 pgs.
Muller et al., "Adding Physics to Animated Characters with Oriented Particles", Workshop on Virtual Reality Interaction and Physical Simulation VRIPHYS (2011), 10 pgs.
Muller et al., "Real Time Dynamic Fracture with Columetric Approximate Convex Decompositions", ACM Transactions of Graphics, Jul. 2013, 11 pgs.
Muller et al., "Position Based Dymanics", VRIPHYS 2006, Oct. 21, 2014, Computer Graphics, Korea University, 23 pgs.
Musse, Soraia Raupp, and Daniel Thalmann. "Hierarchical model for real time simulation of virtual human crowds." IEEE Transactions on Visualization and Computer Graphics 7.2 (2001): 152-164.
Nguyen et al., "Adaptive Dynamics With Hybrid Response," 2012, 4 pages.
O'Brien et al., "Graphical Modeling and Animation of Brittle Fracture", GVU Center and College of Computing, Georgia Institute of Technology, Reprinted from the Proceedings of ACM SIGGRAPH 99, 10 pgs, dated 1999.
Orin et al., "Centroidal dynamics of a humanoid robot," Auton Robot, vol. 35, pp. 161-176, 2013, 18 pages.
Parker et al., "Real-Time Deformation and Fracture in a Game Environment", Eurographics/ACM SIGGRAPH Symposium on Computer Animation (2009), 12 pgs.
Pelechano, Nuria, Jan M. Allbeck, and Norman I. Badler. "Controlling individual agents in high-density crowd simulation." Proceedings of the 2007 ACM SIGGRAPH/Eurographics symposium on Computer animation. Eurographics Association, 2007. APA.
Rivers et al., "FastLSM: Fast Lattice Shape Matching for Robust Real-Time Deformation", ACM Transactions on Graphics, vol. 26, No. 3, Article 82, Publication date: Jul. 2007, 6 pgs.
Ruiz, Sergio, et al. "Reducing memory requirements for diverse animated crowds." Proceedings of Motion on Games. ACM, 2013.
Rungjiratananon et al., "Elastic Rod Simulation by Chain Shape Matching withTwisting Effect" SIGGRAPH Asia 2 010, Seoul, South Korea, Dec. 15-18, 2010, ISBN 978-1-4503-0439-9/10/0012, 2 pgs.
Seo et al., "Compression and Direct Manipulation of Complex Blendshape Models", Dec. 2011, in 10 pgs.
Sifakis, Eftychios D., "FEM Simulations of 3D Deformable Solids: A Practioner's Guide to Theory, Discretization and Model Reduction. Part One: The Classical FEM Method and Discretization Methodology", SIGGRAPH 2012 Course, Version 1.0 [Jul. 10, 2012], 50 pgs.
Stomakhin et al., "Energetically Consistent Invertible Elasticity", Eurographics/ACM SIGRAPH Symposium on Computer Animation (2012), 9 pgs.
Thalmann, Daniel, and Soraia Raupp Musse. "Crowd rendering." Crowd Simulation. Springer London, 2013. 195-227.
Thalmann, Daniel, and Soraia Raupp Musse. "Modeling of Populations." Crowd Simulation. Springer London, 2013. 31-80.
Treuille, A. et al., "Near-optimal Character Animation with Continuous Control", University of Washington, 2007, 7 pgs.
Ulicny, Branislav, and Daniel Thalmann. "Crowd simulation for interactive virtual environments and VR training systems." Computer Animation and Simulation 2001 (2001 ): 163-170.

(56) References Cited

OTHER PUBLICATIONS

Vaillant et al., "Implicit Skinning: Real-Time Skin Deformation with Contact Modeling", (2013) ACM Transactions on Graphics, vol. 32 (n° 4). pp. 1-11. ISSN 0730-0301, 12 pgs.

Vigueras, Guillermo, et al. "A distributed visualization system for crowd simulations." Integrated Computer-Aided Engineering 18.4 (2011 ): 349-363.

Wu et al., "Goal-Directed Stepping with Momentum Control," Eurographics/ ACM SIGGRAPH Symposium on Computer Animation, 2010, 6 pages.

* cited by examiner

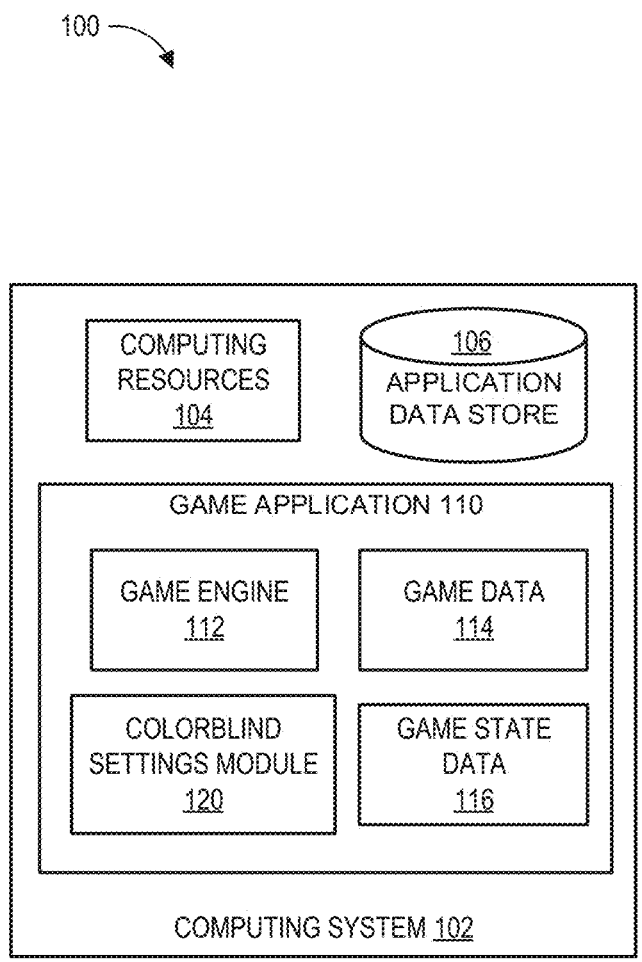
FIG. 1 - System Overview

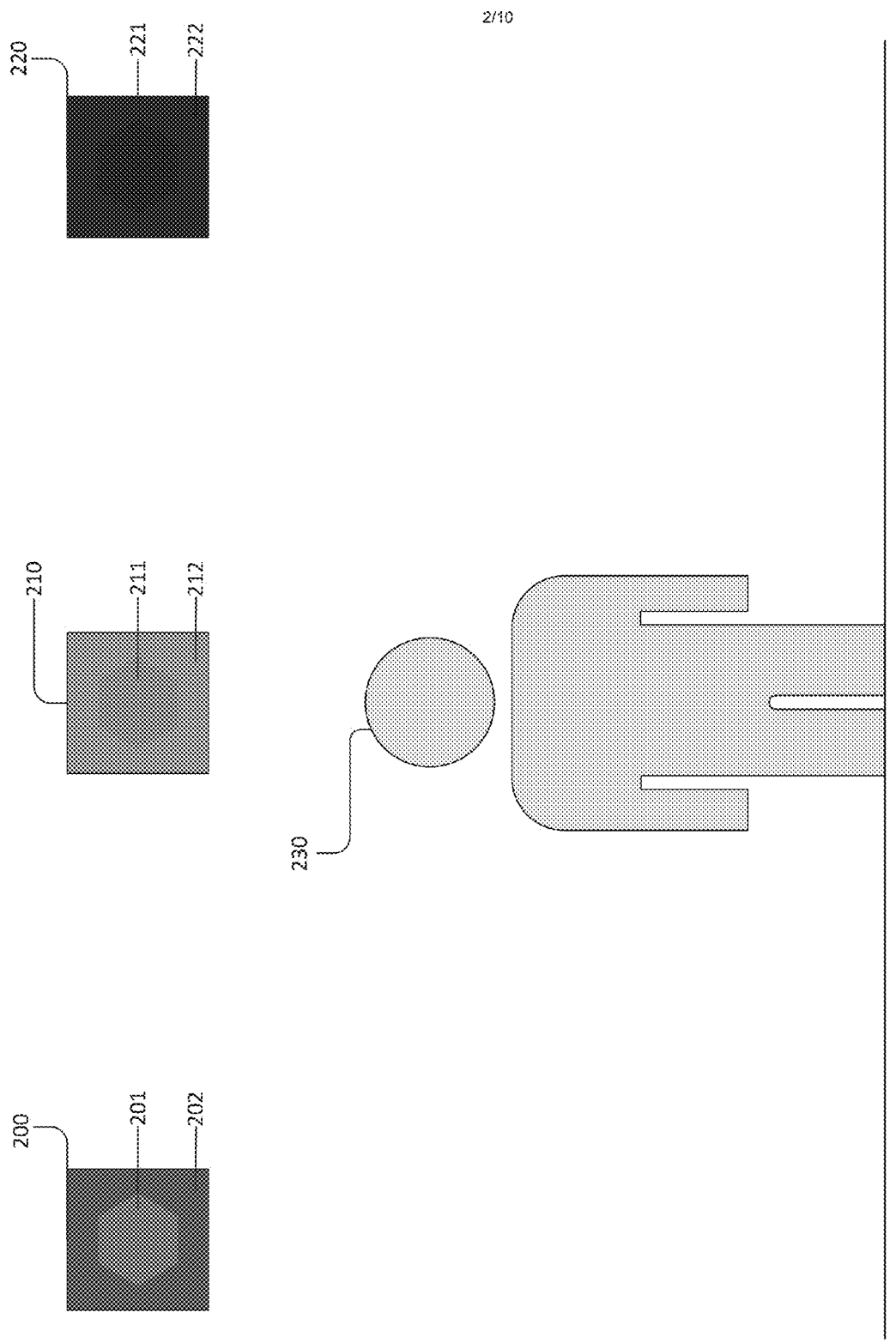
FIG. 2A - Color Blindness Indication Objects

Protanopia Perception
203
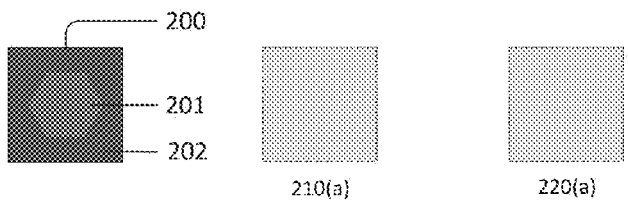
Deuteranopia Perception
213
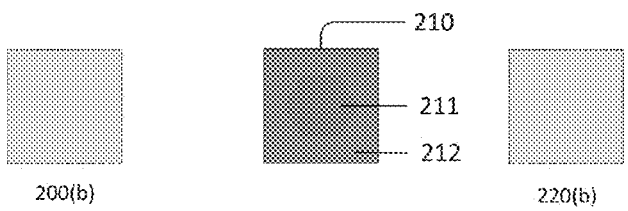
Tritanopia Perception
223
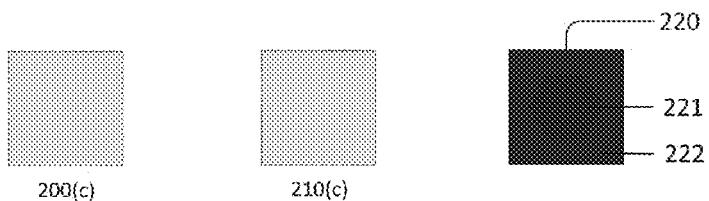
FIG. 2B - Dichromatic Perception of Color Blindness
Indication Objects

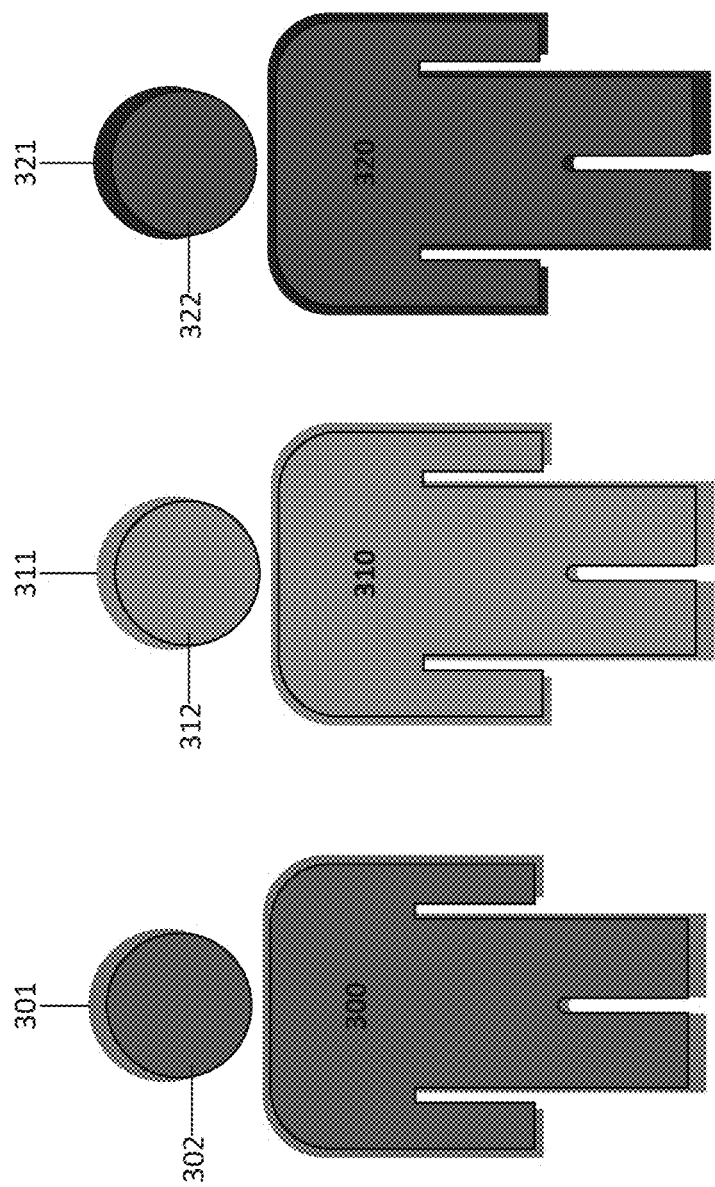
FIG. 3A - Color Blind Targets

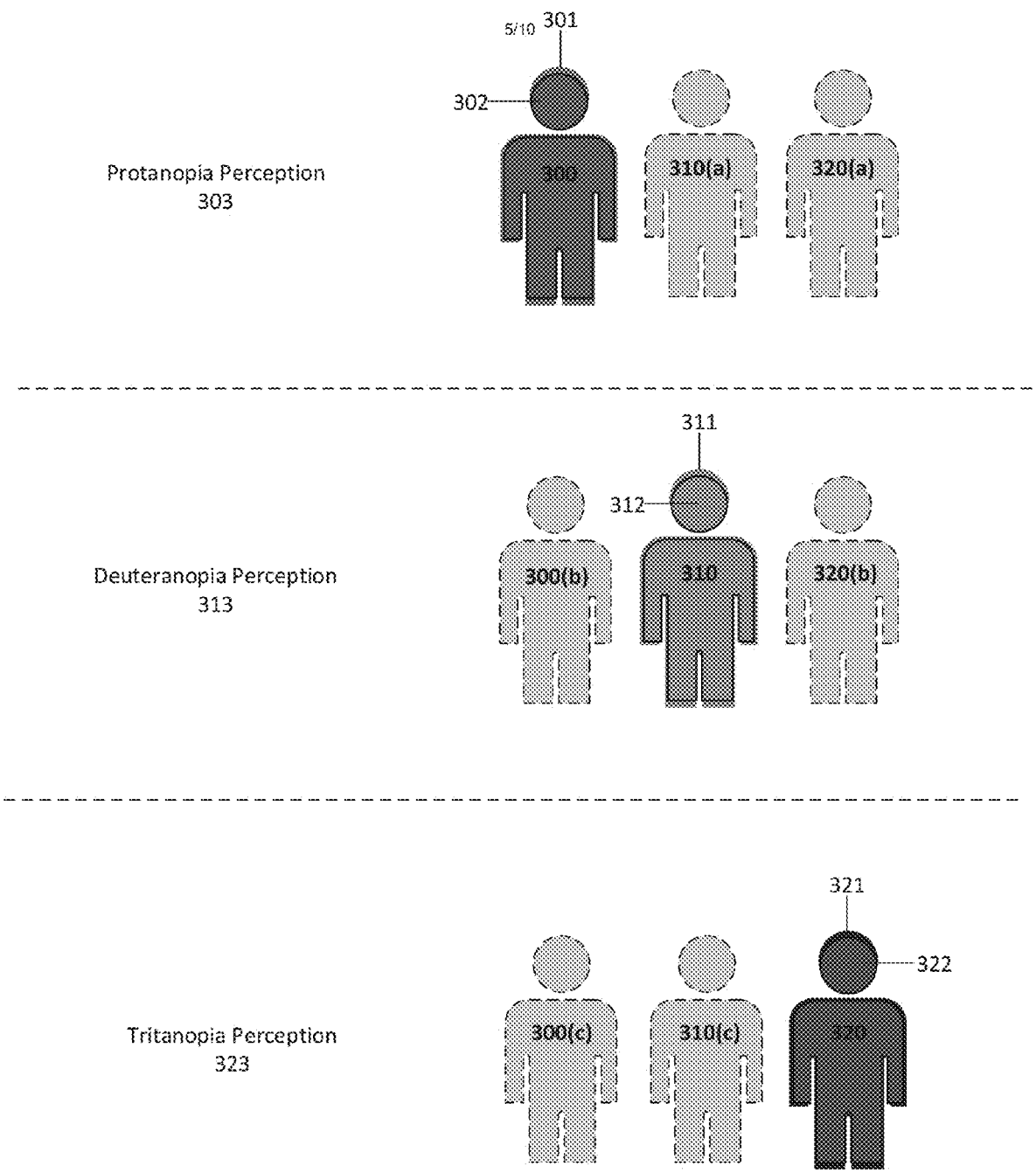
FIG. 3B - Dichromatic Perception of Color Blind Targets

Protanopia Color Blind Target Set
400
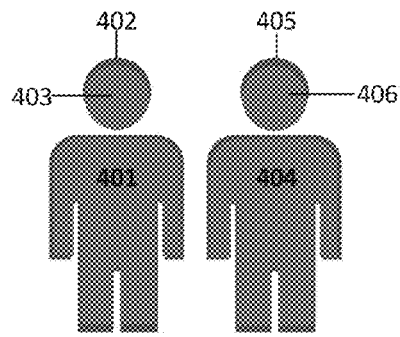
Deuteranopia Color Blind Target Set
410
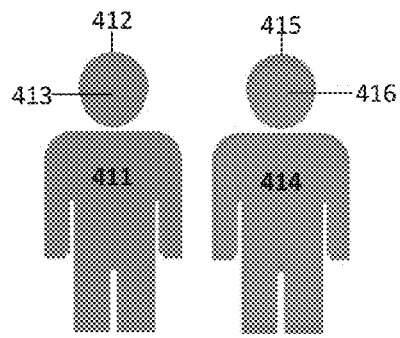
Tritanopia Color Blind Target Set
420
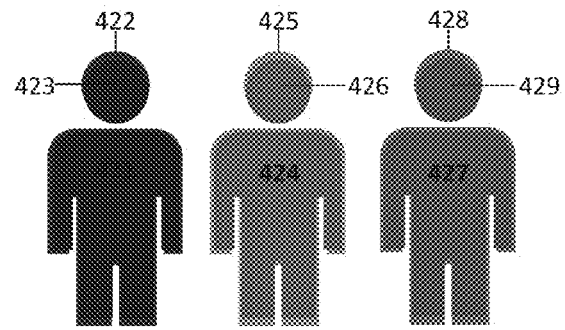
FIG. 4A – Color Blind Target Sets

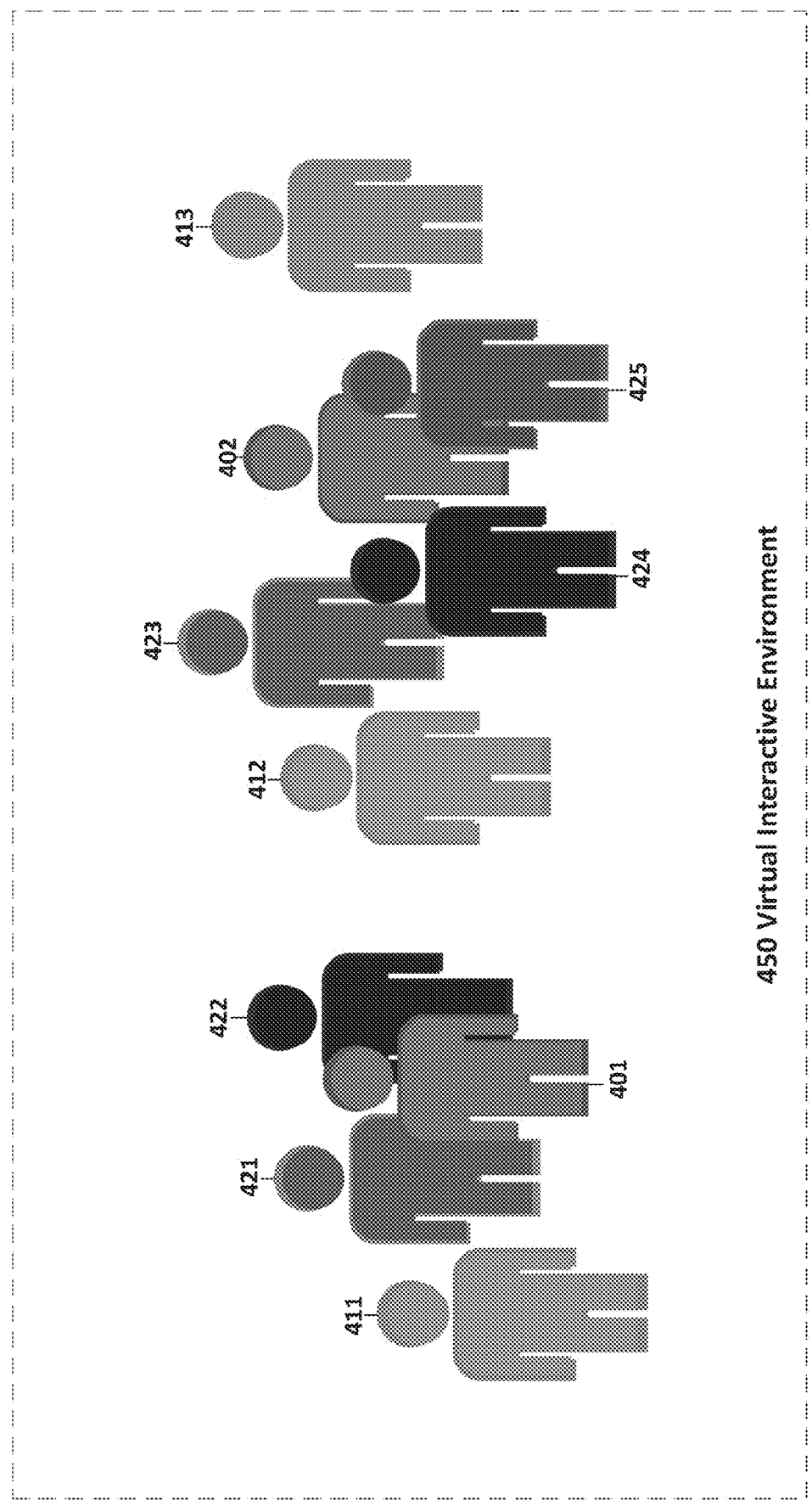
FIG. 4B - Color Blind Target Set Generation

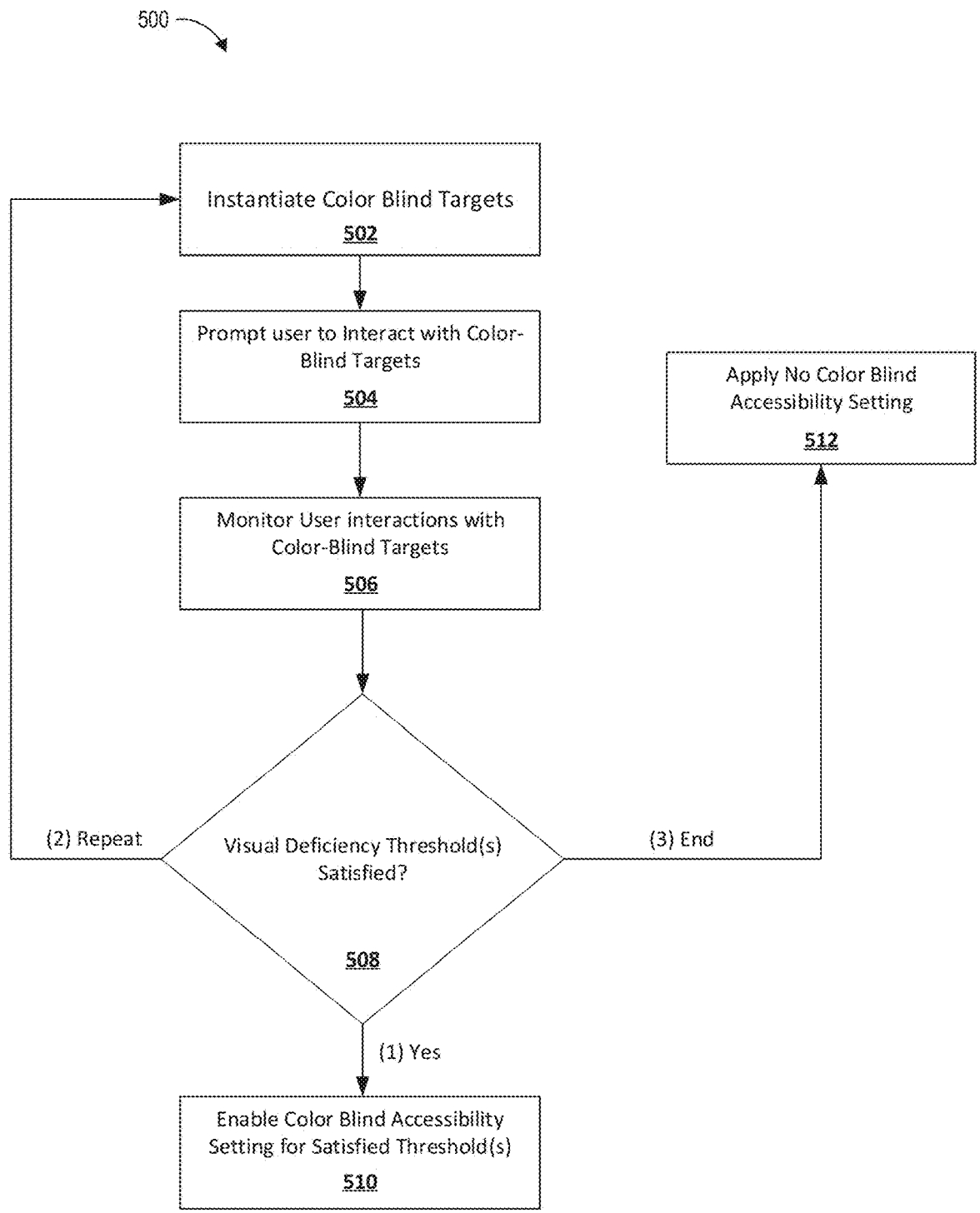
FIG. 5A - Color Blind Accessibility Diagnostic Process

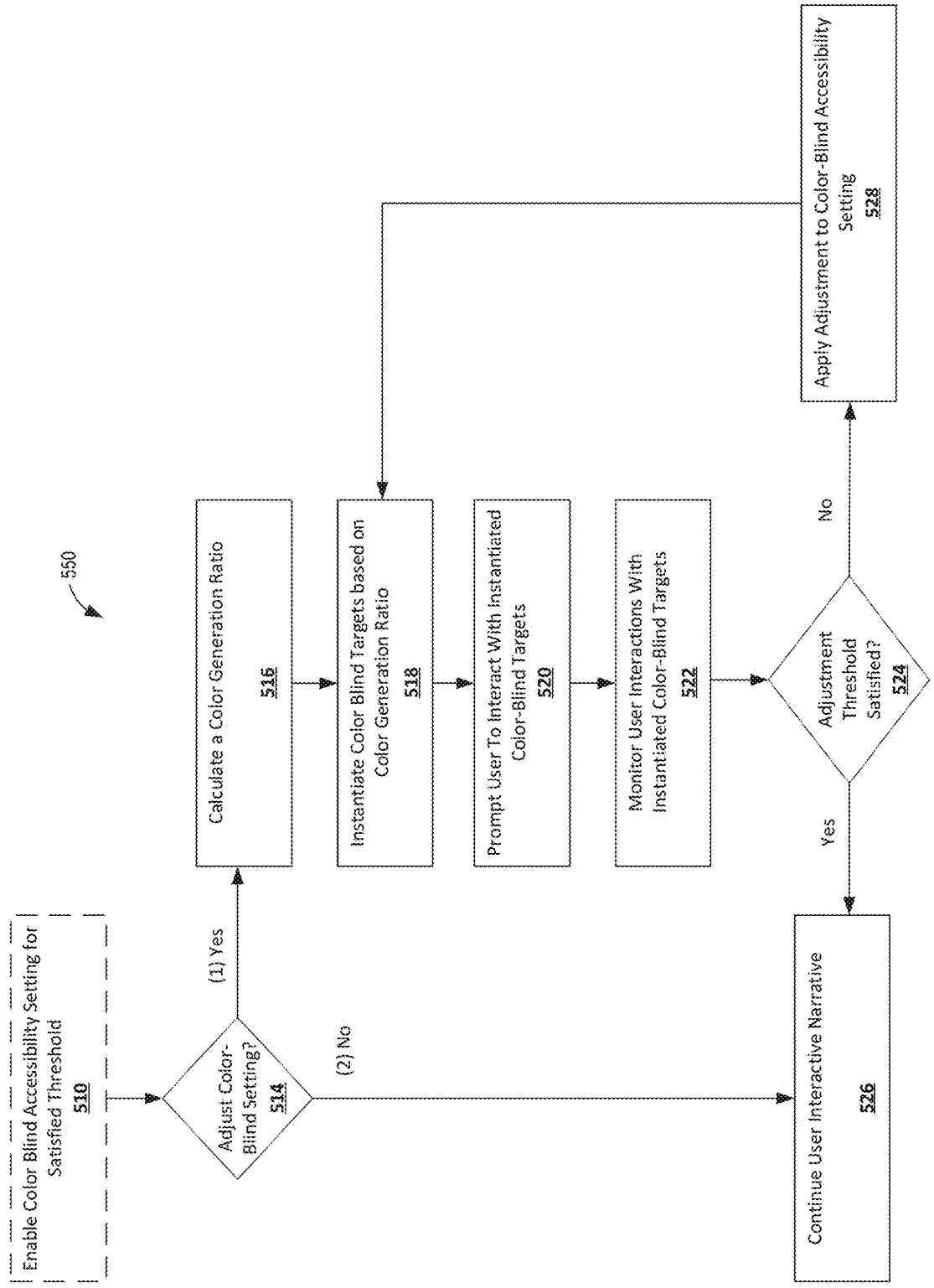
FIG. 5B - Color Blind Accessibility Adjustment Process

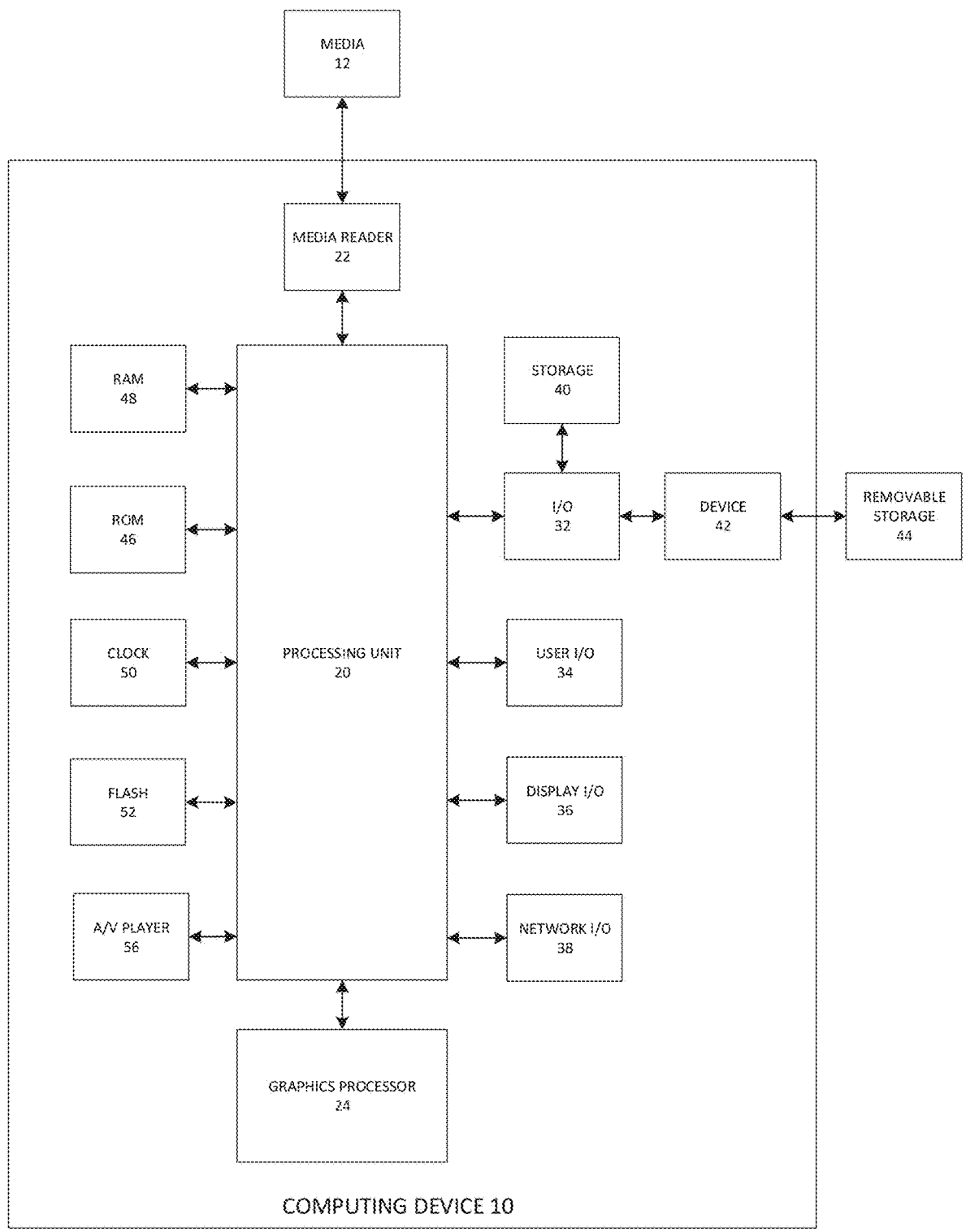
FIG. 6 - Computing System

COLOR BLINDNESS DIAGNOSTIC SYSTEM

BACKGROUND

Modern virtual environments, such as video games, often presume a user does not require modifications for color blind accessibility. Typically, the settings of a virtual environment, including those for color blind accessibility, are unavailable during the introduction of a user interactive narrative. Due to this limitation, color blind users of a video game often miss key visual cues for navigating and progressing through the user interactive narrative within a virtual environment.

SUMMARY OF EMBODIMENTS

The present disclosure provides a system to utilize color blindness indication objects to automatically determine, enable, and adjust color blind accessibility settings during a gameplay session of a video game. Aspects of the present disclosure can help to address the problem of enablement of color blind accessibility settings within a video game. Aspects of the present disclosure also address the adjustment of dichromatic color blind accessibility settings within the course of a user interactive narrative of a virtual environment.

In some embodiments, a virtual environment is configured to determine a user's need for the enablement of a dichromatic color blind (i.e., protanopia, deuteranopia, or tritanopia) accessibility setting within the course of an interactive narrative. A virtual color blindness indication object is a virtual object with colors that are visibly distinguishable within a dichromatic visual spectrum, such as protanopia, deuteranopia, or tritanopia.

In some embodiments, a user interactive narrative includes an objective that prompts a user to interact with one or more virtual color blindness indication objects that the user perceives as having distinguishable colors. Based on a user's interaction with particular virtual color blindness indication objects during a gameplay session, the system can automatically determine a type of dichromatic visual deficiency of a color blind user.

In some embodiments, a user interactive narrative within a video game includes an objective that prompts a user to interact with one or more sets of virtual color blindness indication objects. Sets of virtual color blindness indication objects can be categorized by a dichromatic visual deficiency type. A user's interaction with virtual color blindness indication objects of a set can be used to determine a type of dichromatic visual deficiency.

In some embodiments, a virtual color blindness indication object is a pregenerated virtual object capable of being dynamically instantiated in the course of a user interactive narrative within a virtual environment. In some embodiments, at least one virtual color blindness indication object for each dichromatic visual deficiency type is instantiated during an objective that prompts a user to interact with one or more virtual color blindness indication objects for accurately determining a user's dichromatic visual deficiency type.

In some embodiments, one or more thresholds of interaction are utilized for the determination, enablement, and adjustment of a dichromatic color blind accessibility setting. In one embodiment, a threshold for each dichromatic visual deficiency is defined. In some embodiments, a user meeting the threshold of interaction for a dichromatic visual deficiency type causes the system to determine and enable the dichromatic color blind accessibility setting a user requires.

In alternative embodiments, additional virtual color blindness indication objects are instantiated within the virtual environment for determining an adjustment to the parameters of an enabled dichromatic color blind accessibility setting.

One embodiment includes a computer-implemented method for determining a visual deficiency type of a user during a gameplay session of a game application, the method comprising: by the game application configured by machine-readable instructions executable on at least one hardware computing device, instantiating one or more virtual color blindness indication objects categorized to a visual deficiency type, wherein each of the one or more virtual color blindness indication objects includes a set of colors that are visibly distinguishable within a defined visual spectrum; prompting user interaction with the one or more virtual color blindness indication objects; monitoring the user interaction with the one or more virtual color blindness indication objects; determining if the user interaction with the one or more virtual color blindness indication objects satisfies a visual deficiency threshold; enabling, a color blind accessibility setting based on the visual deficiency threshold satisfied by the user interaction with the one or more virtual color blindness, wherein the color blind accessibility session adjusts the colors used for rendering frames during runtime of the game application.

Various embodiments of the method may include one, all, or any combination of the following features. In some embodiments, the visual deficiency types include protanopia, deuteranopia, and tritanopia. In some embodiments, the virtual color blindness indication objects are a part of a defined dichromatic visual deficiency type set. In some embodiments, the colors of a virtual color blindness indication object form a perceivable pattern within a single dichromatic visual spectrum. In some embodiments, the game application designates a virtual location within the virtual environment for instantiating virtual color blindness indication objects. In some embodiments, prompting user interaction with the one or more virtual color blindness objects occurs after arrival of a virtual entity controlled by the user at the designated virtual location within the virtual environment. In some embodiments, monitoring user interaction further comprises categorizing user interaction with virtual color blindness indication objects by visual deficiency type. In some embodiments, a visual deficiency threshold requires a degree of user interaction with virtual color blindness indication objects categorized to the visual deficiency type. In some embodiments, the method includes calculating a color generation ratio based on user interactions with virtual color blindness indication objects; instantiating one or more virtual color blindness indication object sets based on the color generation ratio; prompting the user to interact with the one or more virtual color blindness indication objects; monitoring user interaction with the one or more virtual color blindness indication objects; determining if the user interaction with the one or more virtual color blindness indication objects satisfies an adjustment threshold; and adjusting the dichromatic visual deficiency setting in response to the user satisfying an adjustment threshold. In some embodiments, causing the virtual environment to adjust the color blind accessibility setting includes applying daltonization. In some embodiments, a color generation ratio comprises values representing colors within a dichromatic visual deficiency spectrum.

One embodiment includes a system comprising: at least one hardware processor configured with machine-readable instructions executable on a computing device that configure the at least one hardware processor to: execute a game application, the game application including a virtual environment; instantiate one or more virtual color blindness indication objects categorized to a dichromatic visual deficiency type within the virtual environment, wherein each of the one or more virtual color blindness indication objects includes a set of colors that are visibly distinguishable within the categorized dichromatic visual spectrum; prompt user interaction with the one or more virtual color blindness indicate on objects; monitor the user interaction with the one or more virtual color blindness indication objects; determine if the user interaction with the one or more virtual color blindness indication objects satisfies a dichromatic visual deficiency threshold; enable a dichromatic color blind accessibility setting based on the dichromatic visual deficiency threshold satisfied by the user interaction with the one or more virtual color blindness indication objects categorized to a dichromatic visual deficiency type, wherein the color blind accessibility session adjusts the colors used for rendering frames during runtime of the game application.

Various embodiments of the system may include one, all, or any combination of the following features. In some embodiments, the categorized dichromatic visual type includes protanopia, deuteranopia, and tritanopia. In some embodiments, the one or more virtual color blindness indication objects belong to a set. In some embodiments, the game application designates a virtual location within the virtual environment for instantiating virtual color blindness indication objects. In some embodiments, the colors of a virtual color blindness indication object form a perceivable pattern within a single dichromatic visual spectrum. In some embodiments, arrival of a virtual entity controlled by the user at the designated virtual location within the virtual environment causes the prompting user interaction with the one or more virtual color blindness indication objects. In some embodiments, the machine-readable instructions are further configured to categorize user interaction with virtual color blindness indication objects by visual deficiency type when monitoring user interaction. In some embodiments, each dichromatic visual deficiency threshold requires a degree of user interaction with the one or more virtual color blindness indication objects categorized to the defined visual deficiency type. In some embodiments, the machine-readable instructions are further configured to: calculate a color generation ratio based on user interactions with virtual color blindness indication objects; instantiate one or more virtual color blindness indication object sets based on the color generation ratio; prompt the user to interact with the one or more virtual color blindness indication objects; monitor user interaction with the one or more virtual color blindness indication objects; determine if the user interaction with the one or more virtual color blindness indication objects satisfies an adjustment threshold; and adjust the dichromatic visual deficiency setting in response to the user satisfying an adjustment threshold.

DESCRIPTION OF DRAWINGS

The patent or application file contains at least one drawing executed in color. Copies of this patent or patent application publication with color drawing(s) will be provided by the Office upon request and payment of the necessary fee.

The present application is directed to color blindness and the systems and methods for rendering virtual objects using specific colors that are used to determine color blindness. Black and white drawings cannot illustrate differences in colors that are illustrated in the application. For example, black and white versions of FIGS. 2A, 2B, 3A, 3B, 4A, and 4B make it impossible for the reader to distinguish between the different colors associated the types of color blindness discussed in the application. Thus, Applicant believes that color drawings are necessary as the only practical medium by which to disclose the subject matter sought to be patented in the accompanying utility patent application.

FIG. 1 illustrates an embodiment of a computing system executing game application including a color blindness diagnostic system.

FIG. 2A illustrates embodiments of color blindness indication lights within a virtual environment.

FIG. 2B illustrates examples of dichromatic visual perceptions of color blindness indication objects.

FIG. 3A illustrates examples of color blind indication objects in a virtual environment.

FIG. 3B illustrates examples of dichromatic visual perceptions of color blind indication objects.

FIG. 4A illustrates examples of color blind target sets.

FIG. 4B illustrates examples of a color blind target set instantiated within a virtual environment.

FIG. 5A illustrates an embodiment of a block diagram of a color blindness diagnostic process.

FIG. 5B depicts an embodiment of a block diagram of the dichromatic color blind accessibility setting adjustment process.

FIG. 6 depicts a block diagram of an illustrative computer system operating in accordance with examples of the invention.

DETAILED DESCRIPTION

The detailed description and figures illustrated are used by way of example, not limitation, to demonstrate some configurations of virtual color blindness indication objects (hereinafter CBIOs, and singularly as CBIO) within a virtual environment.

I. System Overview

FIG. 1 illustrates an embodiment of a computing environment 100 for implementing a executing game application including a color blindness diagnostic system. The environment 100 includes a user computing systems 102.

II. Computing System

The computing system 102 includes computing resources 104 and an application data store 106. The user computing system 102 may have varied local computing resources 104 such as central processing units and architectures, memory, mass storage, graphics processing units, communication network availability and bandwidth, and so forth. Further, the user computing system 102 may include any type of computing system. For example, the user computing system 102 may be any type of computing device, such as a desktop, laptop, video game platform/console, television set-top box, television (for example, Internet TVs), network-enabled kiosk, car-console device, computerized appliance, wearable device (for example, smart watches and glasses with computing functionality), and wireless mobile devices (for example, smart phones, PDAs, tablets, or the like), to name a few. A more detailed description of an embodiment of a computing system 102 is described below with respect to FIG. 6.

a. Game Application

The computing system 102 can include a game application 110 installed thereon. The user computing system 102 can execute a game application 110 based on software code stored at least in part in the application data store 106. The game application 110 may also be referred to herein as a video game, a game, game code or a game program. A game application 110 should be understood to include software code that a computing device 102 can use to provide a game for a user to play. A game application 110 may include software code that informs a computing device 102 of processor instructions to execute, but may also include data used in the playing of the game, such as data relating to game simulation, rendering, animation, and other game data. In the illustrated embodiment, the game application 110 includes a game engine 112, game data 114, and game state data 116. When executed, the game application 110 is configured to generate a virtual environment for a user to interface with the game application 110.

In some embodiments, the user computing system 102 can execute machine readable instructions that are configured to execute the game application 110, such as a video game, stored on a data store on the user computing system (for example, application data store 106). The game application 110 may be stored or executed in a distributed environment using a client/server architecture. For example, the user computing system 102 may execute a portion of a game application 110 and a server may execute another portion of the game application 110. For instance, the game application 110 may be a competitive multiplayer online game, such as a battle royale type game, that includes a client portion executed by the user computing system 102 and a server portion executed by one or more application host systems. For the present discussion, the game application 110 can execute locally on the user computing system 102 or can execute as a distributed application that includes a portion that executes on the user computing system 102 and a portion that executes on at least one or more application host systems.

i. Game Engine

During operation, the game engine 112 executes the game logic, controls execution of the simulation of gameplay, and controls rendering within the game application 110. In some cases, the game engine 112 controls characters, the environment, execution of the gameplay, how the game progresses, or other aspects of gameplay based on one or more stored rule sets. For example, the game engine 112 can monitor gameplay and detect or determine a current runtime state of the game application 110. Based at least in part on the current runtime state of the game application, the game engine 112 applies a rule set to control the characters or the environment.

In some embodiments, the game engine 112 can include a simulation engine and a presentation engine. The simulation engine executes the game logic and controls execution of the gameplay simulation. The presentation engine controls execution of presentation of the gameplay and rendering of frames. In some embodiments, the game engine 112 can execute the functionality of the simulation engine and the presentation engine using different engines and/or processes within the game application.

The simulation engine can control execution of individual virtual components, virtual effects or virtual objects within the game application 110. The simulation engine can manage and determine character movement, character states, collision detection, derive desired motions for characters based on collisions, or the like. Input device(s) allow for user input to be received from the user in order to control aspects of the game application according to rule sets. The simulation engine receives the user inputs and determines character events, such as actions, collisions, runs, throws, attacks and other events appropriate for the game. The character events can be controlled by character movement streams that determine the appropriate motions the characters should make in response to events. The simulation engine can interface with a physics engine that can determine new poses for the characters. The physics engine can have as its inputs, the skeleton models of various characters, environmental settings, character states such as current poses (for example, positions of body parts expressed as positions, joint angles or other specifications), and velocities (linear or angular) of body parts and motions provided by a character movement module, which can be in the form of a set of force/torque vectors for some or all body parts. From this information, the physics engine generates new poses for the characters using rules of physics and those new poses can be used to update character states.

The simulation engine can output graphical state data (e.g., game state data 114) that is used by presentation engine to generate and render frames within the game application 110. In some embodiments, each virtual object can be configured as a state stream process that is handled by the simulation engine. Each state stream process can generate graphical state data for the presentation engine. For example, the state stream processes can include emitters, lights, models, occluders, terrain, visual environments, and other virtual objects with the game application 110 that affect the state of the game.

The presentation engine can use the graphical state data to generate and render frames for output to a display within the game application 110. The presentation engine can combine the virtual objects, such as virtual characters, animate objects, inanimate objects, background objects, lighting, reflection, and the like, in order to generate a full scene and a new frame for display. The presentation engine can take into account the surfaces, colors textures, and other parameters of the virtual objects. The presentation engine can then combine the virtual objects (for example, lighting within the virtual environment and virtual character images with inanimate and background objects) to generate and render a frame. During runtime, the game engine can output many frames per second (e.g., 30 FPS, 60 FPS, or any other number of frames per second as determined during execution of the game application).

ii. Game Data

The game data 114 can include rule sets, prerecorded motion capture poses/paths, environmental settings, environmental objects, constraints, skeleton models, route information, or other game application information.

Rule sets can be applied by the game engine 112 to control characters, the environment, execution of the gameplay, how the game progresses, or other aspects of gameplay. The rule sets can define the specific way in which players (for example, player characters or non-player characters) or the environment behaves or interacts within the video game. For example, the rules sets can correspond to difficulty levels (for example, easy, normal, hard, novice, expert) of a video game. As another example, the rule sets can control a number of resources available to a player, a number of challenges a player must face to progress through the video game, rules for scoring, possible inputs, actions, events, movement in response to inputs, or the like. Further still, for instance in sports-related video games, the rules set can control a degree of skill or ability of a particular virtual player, team, or coach, or can dictate how virtual entities react to particular in-game situations, such as a breakaway, a 3-on-1 attack, a 3-on-1 defense, or the like. In some cases, rule sets can function as a virtual entities' brain or artificial intelligence.

The rule sets can be described using the concepts of characters, actions, runtime states, and environments. The virtual character in the video game can be a player character, which is controlled by a user, or a non-player character, which is controlled by the game application, and an action can be a move from a set of all possible moves the character can make. For example, in a hockey game, the character can pass (action A) or shoot (action B) the puck, among other possible actions. A runtime state can be described as a concrete and immediate situation in which the character finds itself. For example, the runtime state can be a specific place and moment, such as an instantaneous configuration that puts the character in relation to other significant things like tools, obstacles, enemies or prizes. A virtual environment can be described as the virtual world through which the character interacts with the game application. In general, a rule or rule set can define a character's way of behaving (for example, the character's actions) at a given time, runtime state, and environment.

At least a portion of the game data 114 can be stored in the application data store 106. In some embodiments, a portion of the game data 114 may be received or stored remotely, such as in the data store 134. Game data may be received during runtime of the game application 110. For example, in some cases, one or more rule sets can be received, stored, or applied during runtime of the game application 110.

iii. Game State Information

During runtime of the game application 110, the game application 110 can collect or store game state data 118, which can include a game state, character states, environment states, scene object storage, route information, or information associated with a runtime state of the game application 110. For example, the game state data 118 can identify the state of the game application 110 at a specific point in time, such as a character position, character orientation, character action, game level attributes, and other information contributing to a state of the game application 110. The game state data can include simulation game state data and graphical game state data. The simulation game state data can include game state data that is used by the game engine 112 to execute the simulation of the game application 110. The graphical game state data can include game state data that is generated based on the simulation state data and is used to generate and render frames for output on a display.

iv. Colorblind Diagnostic Module

The colorblind diagnostic module can be configured to make a determination of colorblindness of a user and control a set of predefined or user defined settings for execution and enablement of colorblind settings during execution of the game application. The colorblind diagnostic module 120 can be configured to influence how a game engine 110 renders visuals within the virtual environment. The colorblind diagnostic module 120 can automatically adjust settings within the game application based on execution of processes configured to determine dichromatic color blindness of users. The processes are further described herein, such as in relation to the processes illustrated in FIGS. 5A and 5B.

III. Virtual Environment

As used herein, a virtual environment may include a simulated environment (for example, a virtual space) instanced on a user computing system 102 and/or a server that is accessible by a client (for example, user computing system 102) located remotely from the server, to format a view of the virtual environment for display to a user of the client. The simulated environment may have a topography, express real-time interaction by the user, or include one or more objects positioned within the topography that are capable of locomotion within the topography. In some implementations, the topography may be a two-dimensional topography. In other instances, the topography may be a three-dimensional topography. In some implementations, the topography may be a single node. The topography may include dimensions of the virtual environment, or surface features of a surface or objects that are "native" to the virtual environment. In some implementations, the topography may describe a surface (for example, a ground surface) that runs through at least a substantial portion of the virtual environment. In some implementations, the topography may describe a volume with one or more bodies positioned therein (for example, a simulation of gravity-deprived space with one or more celestial bodies positioned therein). A virtual environment may include a virtual world, but this is not necessarily the case. For example, a virtual environment may include a game space that does not include one or more of the aspects generally associated with a virtual world (for example, gravity, a landscape, etc.). By way of illustration, the well-known game Tetris may be formed as a two-dimensional topography in which bodies (for example, the falling tetrominoes) move in accordance with predetermined parameters (for example, falling at a predetermined speed, and shifting horizontally or rotating based on user interaction).

The game instance of the video game 110 may include a simulated virtual environment, for example, a virtual environment that is accessible by users via clients (for example, user computing systems 102) that present the views of the virtual environment to a user. The virtual environment may have a topography, express ongoing real-time interaction by one or more users or include one or more objects positioned within the topography that are capable of locomotion within the topography. In some instances, the topography may include a two-dimensional topography. In other instances, the topography may include a three-dimensional topography. The topography may include dimensions of the space or surface features of a surface or objects that are "native" to the space. In some instances, the topography may describe a surface (for example, a ground surface) that runs through at least a substantial portion of the space. In some instances, the topography may describe a volume with one or more bodies positioned therein (for example, a simulation of gravity-deprived space with one or more celestial bodies positioned therein). The instance executed by the computer components may be synchronous, asynchronous, or semi-synchronous.

It should be understood the above description of the manner in which state of the virtual environment associated with the video game is not intended to be limiting. The game application 110 may be configured to express the virtual environment in a more limited, or richer, manner. For example, views determined for the video game representing the game state of the instance of the video game may be selected from a limited set of graphics depicting an occurrence in a given place within the video game. The views may include additional content (for example, text, audio, pre-stored video content, or other content) that describes particulars of the current state of the place, beyond the relatively generic graphics. For example, a view may include a generic battle graphic with a textual description of the opponents to be confronted. Other expressions of individual places within the video game are contemplated.

The game engine 112 generates game state data 118 that may be used locally within the game application 110 and may be transmitted to the interactive computing system 130 over network 108. The execution of the instance of the game application 110 may include determining a game state associated with the game application 110. The game state data 118 may facilitate presentation of views of the video game to the users on the user computing systems 102. The game state data 118 may include information defining the virtual environment in which the video game is played. The execution of the game engine is described in further detail herein.

The execution of the game instance may enable interaction by the users with the game application 110 or other users through the interactive computing system 130. The game application 110 may be configured to perform operations in the game instance in response to commands received over network 108 from user computing systems 102. In some embodiments, users may interact with elements in the video game or with each other through the video game.

Users may participate in the video game through client game applications 110 implemented on user computing systems 102 associated with the users. Within the game instance of the video game executed by the game engine 112, the users may participate by controlling one or more of an element in the virtual environment associated with the video game. The user-controlled elements may include avatars, user characters, virtual environment units (for example, troops), objects (for example, weapons, horses, vehicle and so on), simulated physical phenomena (for example, wind, rain, earthquakes, or other phenomena), or other user-controlled elements.

The user-controlled character avatars may represent the users in the virtual environment. The user characters may include heroes, knights, commanders, leaders, generals or any other virtual environment entities that may possess strength, skills, abilities, magic powers, knowledge, or any other individualized attributes. The virtual environment units controlled by the user may include troops or any other game entities that may be trained, recruited, captured, or otherwise acquired by the users in groups or en-mass. The objects controlled by the users may include weapons, vehicles, projectiles, magic items, wardrobes, boots, armor, knapsacks, medicine, healing potion, or any other virtual items that may be employed by the users for interaction within the video game.

The user-controlled element(s) may move through and interact with the virtual environment (for example, user-virtual environment units in the virtual environment, non-user characters in the virtual environment, other objects in the virtual environment). The user controlled elements controlled by or associated with a given user may be created or customized by the given user. The user may have an "inventory" of virtual goods or currency that the user can use (for example, by manipulation of a user character or other user controlled element, or other items) within the virtual environment.

Controls of virtual elements in the video game may be exercised through commands input by a given user through user computing systems 102. The given user may interact with other users through communications exchanged within the virtual environment. Such communications may include one or more of textual chat, instant messages, private messages, voice communications, or other communications. Communications may be received and entered by the users via their respective user computing systems 102. Communications may be routed to and from the appropriate users through server(s).

Execution or performance of the user action by the game engine 112 may produce changes to the game state, which may reflect progresses or results of the user actions. In some examples, state changes caused by the execution of the user actions may be recorded in the application data store 106 or data store 134 to facilitate persistency throughout the instance of the video game. In some examples, execution of the user actions may not produce persistent changes to the game state (for example, a user character jumping forward and backward successively may not produce any perceivable game state changes to other users).

A given user may input commands with specific parameters to undertake specific deeds, actions, functions, spheres of actions or any other types of interactions within the virtual environment. For example, the given user may input commands to construct, upgrade or demolish virtual buildings; harvest or gather virtual resources; heal virtual user-controlled elements, non-player entities or elements controlled by other users; train, march, transport, reinforce, reassign, recruit, or arrange troops; attack, manage, create, demolish or defend cities, realms, kingdoms, or any other virtual environment locations controlled by or associated with the users; craft or transport virtual items; interact with, compete against or along with non-player entities or virtual environment elements controlled by other users in combats; research technologies or skills; mine or prospect for virtual resources; complete missions, quests, or campaigns; exercise magic power or cast spells; or perform any other specific deeds, actions, functions, or sphere of actions within the virtual environment. In some examples, the given user may input commands to compete against elements in an environment within the virtual environment—for example, Player vs. Environment (PvE) activities. In some examples, the given user may input commands to compete against each other within the virtual environment—for example, Player vs. Player (PvP) activities.

The instance of the video game may include virtual entities automatically controlled in the instance of the video game. Such virtual entities may or may not be associated with any user. As such, the automatically controlled virtual entities may be generated or developed by artificial intelligence configured with the game application 110 or server(s) by a provider, administrator, moderator, or any other entities related to the video game. These automatically controlled entities may evolve within the video game free from user controls and may interact with the entities controlled by or associated with the users, other automatically controlled virtual environment entities, as well as the topography of the virtual environment. Certain manifested traits may be associated with the automatically controlled entities in accordance with the artificial intelligence configured with server(s). As used herein, such automatically controlled virtual environment entities in the instance of the video game are referred to as "non-player entities."

In an online game, the instance of the video game may be persistent. That is, the video game may continue on whether or not individual users are currently logged in or participating in the video game. A user that logs out of the video game and then logs back in some time later may find the virtual environment or the video game has been changed through the interactions of other users with the video game during the time the user was logged out. These changes may include changes to the simulated physical space, changes in the user's inventory, changes in other users' inventories, changes experienced by non-user characters, or other changes.

IV. Color Blindness Indication Objects

A CBIO can be any virtual object within a virtual environment that can be used to generate a functional indication that a user is color blind. In one embodiment, a CBIO's functional indication of a user's color blindness is implemented by way of its design, placement, and collision information.

The color scheme of a CBIO is configured to be visibly distinguishable (e.g., contrasting) within a single dichromatic visual spectrum; protanopia, deuteranopia, or tritanopia. One skilled in the art will recognize that each dichromatic visual spectrum has perceivable color limitations, such that a perceivable color frequency (i.e., a specific color) appears differently across each of the dichromatic visual spectrums. Each CBIO can be configured to have colors that are distinguishable to a single dichromatic visual spectrum but not to the other types of dichromatic color blindness. For examples, a CBIO can be configured with two colors of different RGB values (e.g., color frequency) are visibly distinguishable as different colors within the protanopia visual spectrum but are visibly indistinguishable within the deuteranopia and tritanopia visual spectrum. This result can occur when the RGB values (i.e., a visible color frequency) of colors fall within a color frequency range of a dichromatic visual spectrum that represent the same color.

As such, each CBIO can function as an indicator of a user's dichromatic visual deficiency type within the virtual environment. CBIOs designed to be visibly distinguishable within a single (i.e., specific) dichromatic visual spectrum are categorized to the respective dichromatic visual deficiency type. For example, a CBIO with a color design that is visibly distinguishable within the tritanopia visual spectrum is categorized as a tritanopia type CBIO within the virtual environment.

The capacity to create color palettes for CBIO's that are only perceivable to a single dichromatic visual spectrum is achievable due to the color frequency limitations of dichromatic visual spectrums. The colors used for the CBIOs in the figures of the present disclosure are approximations of colors that are only distinguishable within a single dichromatic visual deficiency type: protanopia, deuteranopia, and tritanopia. The color palette for CBIOs need not be limited to the specific colors used in the figures of this disclosure.

Further, the present disclosure illustrates CBIOs with two colors by way simplicity, not limitation. A CBIO need not be limited to a pair of colors that are visibly contrasting within a single dichromatic visual spectrum. Alternative configurations of CBIOs can include one or more colors or arrangements that are visibly contrasting within a single dichromatic visual spectrum. For example, a CBIO may include a specific color design that creates one or more patterns perceivable within a defined dichromatic visual spectrum.

A virtual environment can utilize CBIOs within objectives that require users to interact with CBIOs that are perceivable to the user. Due to the CBIOs design and the physical color frequency limitations of dichromatic visual spectrums, a user who is dichromatically color blind will only distinguish the CBIOs categorized to their specific dichromatic visual deficiency type. A dichromatically color blind user is likely to interact with the CBIOs they can perceive within the virtual environment. The game application can determine an appropriate color blind setting to enable based on the user's interactions with the CBIOs.

For example, a CBIO configured to indicate protanopia color blindness can include colors that are visibly distinguishable within the protanopia visual color spectrum. The CBIO would appear to be indistinguishable within the deuteranopia and tritanopia visual spectrums. As such a color blind user with protanopia color blindness would be capable of perceiving and interacting with the protanopia CBIO.

In some embodiments, a virtual environment can prompt a user to complete an objective that requires user interaction with one or more CBIOs that the user perceives as having a distinguishable color design. The game application can monitor user actions to determine a user's interaction with one or more CBIOs. In some embodiments, objectives requiring user interaction with CBIOs are scripted events that to occur within a user interactive narrative.

By instantiating at least one CBIO categorized to each dichromatic visual deficiency type during an objective, the game application can be configured to determine whether a user is colorblind. A user that is not colorblind may interact with all three CBIOs. In instances where a user have interactions with CBIOs of a single categorized type can indicate a user is dichromatically color blind with respect to the CBIO's categorized dichromatic deficiency type. The utilization of CBIOs can be an advantageous and efficient solution for determining a user's dichromatic visual deficiency within a virtual environment and enabling a corresponding color blindness accessibility setting.

Those skilled in the art can appreciate the myriad of variations for the implementation and configuration of CBIOs within a virtual environment. Variations of CBIO implementation and configuration include, but are not limited to, contrasting one or more colors within a single, or through multiple, virtual objects, characters, environments, terrains, skyboxes, text, pathways, guidelines, destination points, UI elements, or any other virtual or animated renditions that would provide at least one visually distinguishable, or indistinguishable, colored virtual element to a color blind user such that the game application can be configured to determine a user's perceivable color spectrum. As such, one skilled in the art should also recognize that implementations of CBIOs in a virtual environment may be implemented as either dynamic, static, predefined, prefabricated, global, local, remote, volatile, or persistent objects, systems or methods.

A user interactive narrative of a virtual environment is not limited to predefined objectives and experiences that are created by a development team. A user interactive narrative of a virtual environment may include content that is procedurally generated, or user generated. A user interactive narrative of a virtual environment includes, but is not limited to, event sequences such as linear and non-linear story modes, campaigns, tutorials, questions, missions, objectives, and other user completable tasks.

a. Color Blindness Indication Lights

FIG. 2A illustrates example embodiments of color blindness indication objects (items 200, 210, 220) for use within a virtual environment.

In the illustrated embodiment, the CBIOs 200, 210, and 220 are categorized by their functional indication of dichromatic visual deficiency types; protanopia, deuteranopia, and tritanopia respectively. The CBIOs (items 200, 210, 220) include an outer housing (items 201, 211, 221) and inner light elements (items 202, 212, and 222). Each CBIO is populated with colors that are visibly contrasting with one another within the dichromatic visual spectrum that correspond to the categorized dichromatic visual deficiency type of the CBIO.

To illustrate, CBIO 200 includes an outer housing 201 colored pink and inner light 202 colored orange. The difference of color between the outer housing 201 and the inner light 202 can be distinguished within the protanopia visual spectrum, as such CBIO 200 is categorized as a protanopia indicator. CBIO 210 includes an outer housing 211 colored light green and an inner light 212 colored bright green. The difference of color between the outer housing 211 and the inner light 212 can distinguished within the deuteranopia visual spectrum, as such CBIO 210 is categorized as a deuteranopia indicator. CBIO 220 includes an outer housing 221 colored purple and inner light 222 colored dark blue. The difference of color between the outer housing 221 and the inner light 222 can distinguished within the tritanopia visual spectrum, as such CBIO 220 is categorized as a tritanopia indicator.

CBIOs (items 200, 210, 220) can be used in a virtual environment as functional indicators for a dichromatic visual deficiency type. An appropriate dichromatic color blind accessibility setting for a dichromatic color blind user can be determined and enabled based on a user's interaction with the CBIOs during a gameplay session.

For example, during a user interactive narrative, the user may be prompted by the virtual environment to interact with CBIOs (items 200, 210, or 220) that the user perceives as having distinguishable colored elements. Due to the specific color palette of the CBIOs (items 200, 210, 220), a color blind user with a dichromatic visual deficiency will generally only be able to perceive one CBIO as having distinguishable colored elements. As such, the virtual character 230 can be utilized by the user to interact with CBIOs. Based on the interactions, the game application can determine and enable the appropriate color blind accessibility setting. In some embodiments, the game application can use the viewpoint of the user within the virtual environment. For example, the game application may monitor the amount of time the that user directs their view to each CBIO.

FIG. 2B illustrates the dichromatic perceptions of CBIOs. FIG. 2A is divided into three subgroups to illustrate each dichromatic perception of the CBIOs (items 200, 210, 220).

The protanopia perception subgroup 203 illustrates the perspective of a protanopia color blind user within the virtual environment. The CBIO 200 would appear as having distinguishable colors in the outer housing 201 and inner light 202 within the protanopia color spectrum. The colors used for the outer housing (items 211,221) and inner light (212,222) elements of CBIO 210 and 220 can blend together within the protanopia visual spectrum, making CBIO 210 and 220 appear as one solid color within the protanopia visual spectrum, as illustrated by 210(a) and 220(a).

The deuteranopia perception subgroup 213 illustrates the perspective of a deuteranopia color blind user within the virtual environment. The CBIO 210 would appear as having distinguishable colors in the outer housing 211 and inner light 212 within the deuteranopia color spectrum. The colors used for the outer housing (items 201,221) and inner light (202,222) elements of CBIO 200 and 220 can blend together within the deuteranopia visual spectrum, making CBIO 200 and 220 appear as one solid color within the deuteranopia visual spectrum, as illustrated by 200(b) and 220(b).

The tritanopia perception subgroup 223 illustrates the perspective of a tritanopia color blind user of the virtual environment, CBIO 220 would appear as having distinguishable colors in the outer housing 221 and inner light 222 within the tritanopia color spectrum. The colors used for the outer housing (items 201,211) and inner light (202,212) elements of CBIO 200 and 210 can blend together within the tritanopia visual spectrum, making CBIO 200 and 210 appear as one solid color within the tritanopia visual spectrum, as illustrated by 200(c) and 210(c).

Utilizing CBIOs within the virtual environment can provide a mechanism by which a dichromatic color blind user can perceive and distinguish particular virtual objects amongst a plurality of virtual objects. The interactions that a dichromatic color blind user makes with the CBIOs can be used to determine the visual deficiency of the user and enable the appropriate color blind accessibility settings.

b. Color Blindness Indication Targets

FIGS. 3A and 3B illustrate additional examples of CBIOs. FIG. 3A illustrates example color blind targets 300, 310, and 320. Similar to the lights in FIG. 2A, Color blind targets 300, 310, and 320 are categorized by their dichromatic visual deficiency types; protanopia, deuteranopia, and tritanopia respectively. Each CBIO has two colors that visibly contrast with one another. In this embodiment, the body (items 302, 312, 322) and outer shield elements (items 301, 311, and 321) of each CBIO (items 300, 310, 320) are populated with colors that are visibly contrasting with one another based on a dichromatic visual spectrum that corresponds to the categorized dichromatic visual deficiency type. CBIO 300 is associated with the protanopia visual spectrum, CBIO 310 is associated with the deuteranopia visual spectrum, and CBIO 320 is associated with the tritanopia visual spectrum.

FIG. 3B illustrates the dichromatic perceptions of color blind targets. FIG. 3B is divided into three subgroups to illustrate each dichromatic perception of the color blind targets (items 300, 310, 320 from FIG. 3). As further discussed in FIG. 2B, a CBIO having colors within a dichromatic visual spectrum will be distinguishable to a user, whereas colors within the other dichromatic visual spectrums can blend together as a single color.

The color blind targets (items 300, 310, and 320) are illustrated as humanoids by way of example. As a CBIO, color blind targets need not be limited to a humanoid form and may be any virtual object or graphical representation within a virtual environment.

c. Color Blindness Indication Object Sets

FIGS. 4A and 4B illustrate additional examples of CBIOs. FIG. 4A is divided into three subgroups to illustrate the set for each dichromatic visual deficiency type. (items 400, 410, 420). The protanopia, deuteranopia, and tritanopia color blind target sets (items 400, 410, 420 respectively) each contain CBIOs that are distinguishable within a respective dichromatic visual spectrum. Color blind targets 400, 410, and 420 are categorized by their dichromatic visual deficiency types; protanopia, deuteranopia, and tritanopia respectively. Each CBIO has two colors that visibly contrast with one another. In this embodiment, the CBIOs within 410 are humanoid shaped virtual objects (items 401, 404, 411, 414, 421, 424, 427) with inner bodies that are a first color (items 403, 406, 413, 416, 423, 426, 429) and outer shields that are a second color (items 402, 405, 412, 415, 422, 425, 428). The first and second colors are visibly contrasting with one another based on a dichromatic visual spectrum that corresponds to the categorized dichromatic visual deficiency type. CBIO set 400 is associated with the protanopia visual spectrum, CBIO set 410 is associated with the deuteranopia visual spectrum, and CBIO set 420 is associated with the tritanopia visual spectrum.

FIG. 4B illustrates an in-game implementation of color blind target sets in a virtual environment 450 of a game application. In some embodiments, a virtual environment is arranged as a shooting range. The a user be prompted within the virtual environment to interact with color blind targets by shooting at the of virtual color blind indication target that user perceives as having distinguishable colors. In some embodiments, the virtual environment is a field for a sporting event. The virtual environment can prompt a user to interact with the color blind targets by passing a virtual ball towards the virtual color blind indication target that user perceives as having distinguishable colors.

V. Color Blindness Determination Process

FIG. 5A depicts a block diagram of the process 500 for determining an appropriate color blind accessibility setting during runtime of a game application.

At block 502, during runtime of the game application, a plurality of CBIO's can be instantiated within the virtual environment. Each CBIO can be associated with a defined type of dichromatic visual deficiency (e.g., protanopia, deuteranopia, or tritanopia). The game application can be configured to instantiate at least one CBIO for each type of dichromatic visual deficiency.

At block 504, the game application can generate prompts or objectives within the virtual environment for the user to interact with one or more CBIOs. The prompt can include instructions for interacting with a CBIO. In some embodiments, the instructions from the prompt of the user objective may specify one or more methods for the user to successfully interact with a CBIO, including, but not limited to, directing the player towards the CBIO, causing a virtual character controlled by a user to make contact with the CBIO in the virtual environment, causing a virtual character controlled by the user to project a virtual object towards the CBIO, generating elements within the virtual environment that enable the user to make a direct selection of a CBIO. In some embodiments, color population of the elements of a CBIO occur during the instantiation of CBIOs. In alternative embodiments, CBIOs elements are baked textures that are predefined during development time.

At block 506, the game application can monitor the user's interaction with the CBIOs. The game application can monitor characteristics of the user's interaction with each CBIO. For example, the game application can determine direct interactions with each CBIO, position of the user within the virtual environment relative to each CBIO, time spent interacting with each CBIO, time spent with the user's viewpoint directed to the CBIO, and other types of interactions within the virtual environment.

At block 508, the game application determines whether the user's interactions with the CBIO's satisfy thresholds for enabling one or more colorblind settings within the game application. The game application can include one or more predefined thresholds of interaction. In some embodiments, predefined thresholds of interaction are an value that indicates a desired level of user interaction with one or more CBIOs. In some embodiments, predefined thresholds of interactions can measure a user's time spent interacting with the CBIO, including, but not limited to, user's time spent causing a virtual character to view, select, destroy, move, modify, or projecting an object towards the CBIO. In some embodiments, predefined thresholds of interactions can measure the degree or extent to which a user interacts with CBIO, including, but not limited to, the accuracy or precession of a user's direct view of a CBIO. The game application can determine if predefined threshold(s) is satisfied based on the analysis of the user's interaction.

If the one or more thresholds for color blindness are not satisfied, the game application can determine whether to continue to monitor the user's interactions the CBIO(s) or to end the color blindness diagnostic process. If user interaction with color blind targets does not satisfy a dichromatic visual deficiency threshold, at (2) the game application will restart or continue the determination process and return to block 502. If user interaction with color blind targets does satisfies each dichromatic visual deficiency threshold, at (3) the virtual environment determines that user is not dichromatically color blind because the user is capable of perceiving every color blind target. The game application will proceed to block 512 and end the determination process and will apply no dichromatic color blind accessibility setting.

At block 510, if the threshold of interaction is satisfied for at least one of the types of color blindness, the game application can automatically enable one or more color blindness settings within the game application. For example, if user interaction with one or more color blind targets satisfies the dichromatic visual deficiency threshold for deuteranopia, the deuteranopia color blind accessibility setting will be enabled. In some embodiments, enablement of a dichromatically accessibility setting causes the virtual environment to allow the user to progress to the next portion of a user interactive narrative.

By enabling the color blindness setting within the game application, the visual output generated and output to the user can be changed to address the type of dichromatic color blindness detected. For example, color palettes used to represent the virtual environment may be shifted or modified. In some embodiments, the game application can generate a recommendation that is presented to the user based on the detected type of dichromatic color blindness. The user can then verify the recommendation and proceed with enabling the color blindness settings. After the settings have been enabled, the process can end. In some embodiments, after enablement of a color blindness setting, the game application can execute a color blindness adjustment process, such as described with respect to process 550 in FIG. 5B.

FIG. 5B depicts a block diagram of the dichromatic color blind accessibility setting adjustment process.

In some embodiments, the game application can execute a color blindness adjustment process after a color blind accessibility setting is enabled in step 510. At block 514, the game application determines whether to adjust the color blind accessibility setting. To determine if an adjustment is required, the game application can analyze the monitored user interactions with color blind targets to identify if the user failed to interact with all color blind targets within a color blind target set. If the user failed to interact with all color blind targets of the color blind target set, the game application may determine that the user is unable to distinguish all color blind targets within a set categorized to their dichromatic visual deficiency type, and the user is likely to continue to find some colors to be indistinguishable even after the enablement of a color blind accessibility setting. This may be due to the natural variance in human perception and/or the variance in colors displayed among different hardware displays.

If no adjustment to the enabled color blind accessibility setting is required, at (2) the game application can proceed to block 526 and allow the user continue the user interactive narrative with the current color blind accessibility setting. If an adjustment to the enabled color blind accessibility setting is determined to be required, at (1) the virtual environment will proceed to block 516.

At block 516, calculate a color blind target set generation ratio based on the monitored user interaction. A color generation ratio is a ratio value that represents the distinguishable colors within the categorized dichromatic visual spectrum of the dichromatic visual deficiency threshold. In some embodiments, the color generation ratio can be configured such that its values represent a range of color frequencies that a user did not previously perceive as being distinguishable. In other embodiments, the color generation ratio can be configured so its value represents specific RBG values. In alternative embodiments, a virtual environment can utilize any number of color generation ratios, each of which being capable of an independent value configuration. The virtual environment can utilize the identified colors from color blind targets determined to be indistinguishable to the user to calculate the color generation ratio.

At block 518, the game application can instantiate color blind targets based on the color generation ratio. In one embodiment, the instantiated color blind targets are CBIOs with elements populated by colors the user found to be indistinguishable. For example, the color generation ration can be used to generate a plurality of CBIOs that are slight color variations based on the indistinguishable colors.

At block 520, the game application can prompt the user to interact with the instantiated color blind targets. At block 522, the game application can monitor user interactions with instantiated color blind targets to determine user's interactions with the adjusted CBIOs.

At block the 524, the game applications determines whether the user's interactions satisfy an adjustment threshold. An adjustment threshold is a value that indicates that a user has interacted with a sufficient amount of instantiated color blind targets that the user has the capacity to distinguish colors within instantiated color blind targets appropriately. If a user satisfies the adjustment threshold, the process can proceed to block 526 and game application can will continue the user interactive narrative with the current color blind accessibility setting.

If an adjustment threshold is not satisfied, the game application can proceed to block 528. At block 528, the game application can apply an adjustment to the color blind accessibility setting. In some embodiments an adjustment to the color blind accessibility setting includes, but is not limited to, post process parameter changes such as daltonization. In preferred embodiments, adjustments to the color blind accessibility setting are made based on monitored user interaction with color blind targets. After application of the adjustment to the color blind accessibility setting, the process can proceed to block 518. The game application can reperform the process to monitor user interactions with the instantiated targets with the adjustment applied. Thereafter, the virtual environment will redetermine if the adjustment threshold is reached at block 524. If not met, an iterative process of adjustments can occur automatically until the user satisfies the adjustment threshold at block 524.

VI. Computing Device

FIG. 6 illustrates an embodiment of computing device 10 according to the present disclosure. Other variations of the computing device 10 may be substituted for the examples explicitly presented herein, such as removing or adding components to the computing device 10. The computing device 10 may include a game device, a smart phone, a tablet, a personal computer, a laptop, a smart television, a car console display, a server, and the like. As shown, the computing device 10 includes a processing unit 20 that interacts with other components of the computing device 10 and external components. A media reader 22 is included that communicates with media 12. The media reader 22 may be an optical disc reader capable of reading optical discs, such as CD-ROM or DVDs, or any other type of reader that can receive and read data from media 12. One or more of the computing devices may be used to implement one or more of the systems disclosed herein.

Computing device 10 may include a separate graphics processor 24. In some cases, the graphics processor 24 may be built into the processing unit 20. In some such cases, the graphics processor 24 may share Random Access Memory (RAM) with the processing unit 20. Alternatively, or in addition, the computing device 10 may include a discrete graphics processor 24 that is separate from the processing unit 20. In some such cases, the graphics processor 24 may have separate RAM from the processing unit 20. Computing device 10 might be a handheld video game device, a dedicated game console computing system, a general-purpose laptop or desktop computer, a smart phone, a tablet, a car console, or other suitable system.

Computing device 10 also includes various components for enabling input/output, such as an I/O 32, a user I/O 34, a display I/O 36, and a network I/O 38. I/O 32 interacts with storage element 40 and, through a device 42, removable storage media 44 in order to provide storage for computing device 10. Processing unit 20 can communicate through I/O 32 to store data. In addition to storage 40 and removable storage media 44, computing device 10 is also shown including ROM (Read-Only Memory) 46 and RAM 48. RAM 48 may be used for data that is accessed frequently.

User I/O 34 is used to send and receive commands between processing unit 20 and user devices, such as keyboards or game controllers. In some embodiments, the user I/O can include a touchscreen. The touchscreen can be capacitive touchscreen, a resistive touchscreen, or other type of touchscreen technology that is configured to receive user input through tactile inputs from the user. Display I/O 36 provides input/output functions that are used to display images. Network I/O 38 is used for input/output functions for a network. Network I/O 38 may be used during execution, such as when a client is connecting to a server over a network.

Display output signals produced by display I/O 36 comprising signals for displaying visual content produced by computing device 10 on a display device, such as graphics, user interfaces, video, and/or other visual content. Computing device 10 may comprise one or more integrated displays configured to receive display output signals produced by display I/O 36. According to some embodiments, display output signals produced by display I/O 36 may also be output to one or more display devices external to computing device 10, such a display 16.

The computing device 10 can also include other features, such as a clock 50, flash memory 52, and other components. An audio/video player 56 might also be used to play a video sequence, such as a movie. It should be understood that other components may be provided in computing device 10 and that a person skilled in the art will appreciate other variations of computing device 10.

Program code can be stored in ROM 46, RAM 48 or storage 40 (which might comprise hard disk, other magnetic storage, optical storage, other non-volatile storage or a combination or variation of these). Part of the program code can be stored in ROM that is programmable (ROM, PROM, EPROM, EEPROM, and so forth), part of the program code can be stored in storage 40, and/or on removable media such as media 12 (which can be a CD-ROM, cartridge, memory chip or the like, or obtained over a network or other electronic channel as needed). In general, program code can be found embodied in a tangible non-transitory signal-bearing medium.

Random access memory (RAM) 48 (and possibly other storage) is usable to store variables and other processor data as needed. RAM is used and holds data that is generated during the execution of an application and portions thereof might also be reserved for frame buffers, application state information, and/or other data needed or usable for interpreting user input and generating display outputs. Generally, RAM 48 is volatile storage and data stored within RAM 48 may be lost when the computing device 10 is turned off or loses power.

As computing device 10 reads media 12 and provides an application, information may be read from media 12 and stored in a memory device, such as RAM 48. Additionally, data from storage 40, ROM 46, servers accessed via a network (not shown), or removable storage media 46 may be read and loaded into RAM 48. Although data is described as being found in RAM 48, it will be understood that data does not have to be stored in RAM 48 and may be stored in other memory accessible to processing unit 20 or distributed among several media, such as media 12 and storage 40.

It is to be understood that the above description is intended to be illustrative, and not restrictive. Many other implementations will be apparent to those of skill in the art upon reading and understanding the above description. The scope of the present disclosure should, therefore, be determined with reference to the appended claims, along with the full scope of equivalents to which such claims are entitled.

In the above description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Some portions of the detailed descriptions above are presented in terms symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.).

What is claimed is:

1. A computer-implemented method for determining a visual deficiency type of a user during a gameplay session of a game application, the method comprising:
by the game application configured by machine-readable instructions executable on at least one hardware computing device,
instantiating a plurality of virtual objects within a virtual environment of the game application, wherein the plurality of virtual objects comprises one or more virtual color blindness indication objects categorized to a visual deficiency type, wherein the one or more virtual color blindness indication objects are located at a designated location within the virtual environment, wherein each of the one or more virtual color blindness indication objects includes a set of colors that are visibly distinguishable within a defined visual spectrum;
rendering the plurality of virtual objects within the virtual environment including the one or more virtual color blindness indication objects;
prompting user interaction with the one or more virtual color blindness indication objects;
monitoring the user interaction with the one or more virtual color blindness indication objects;
determining if the user interaction with the one or more virtual color blindness indication objects satisfies a visual deficiency threshold; and
enabling, a color blind accessibility setting based on the visual deficiency threshold satisfied by the user interaction with the one or more virtual color blindness, wherein the color blind accessibility setting adjusts colors used for rendering frames during runtime of the game application.

2. The method of claim 1, wherein visual deficiency types include protanopia, deuteranopia, and tritanopia.

3. The method of claim 2, wherein the virtual color blindness indication objects are a part of a defined dichromatic visual deficiency type set.

4. The method of claim 1, wherein the colors of a virtual color blindness indication object form a perceivable pattern within a single dichromatic visual spectrum.

5. The method of claim 1, wherein prompting user interaction with the one or more virtual color blindness objects occurs after arrival of a virtual entity controlled by the user at the designated virtual location within the virtual environment.

6. The method of claim 1, wherein monitoring user interaction further comprises categorizing user interaction with virtual color blindness indication objects by visual deficiency type.

7. The method of claim 1, wherein a visual deficiency threshold requires a degree of user interaction with virtual color blindness indication objects categorized to the visual deficiency type.

8. The method of claim 1 further comprising:
calculating a color generation ratio based on user interactions with virtual color blindness indication objects;
instantiating one or more virtual color blindness indication object sets based on the color generation ratio;
prompting the user to interact with the one or more virtual color blindness indication objects;
monitoring user interaction with the one or more virtual color blindness indication objects;

determining if the user interaction with the one or more virtual color blindness indication objects satisfies an adjustment threshold; and adjusting the colorblind accessibility setting in response to the user satisfying the visual deficiency threshold.

9. The method of claim 8 wherein causing the virtual environment to adjust the color blind accessibility setting includes applying daltonization.

10. The method of claim 8 wherein a color generation ratio comprises values representing colors within a dichromatic visual deficiency spectrum.

11. A system comprising:
at least one hardware processor configured with machine-readable instructions executable on a computing device that configure the at least one hardware processor to:
execute a game application, the game application including a virtual environment;
instantiate a plurality of virtual objects within a virtual environment of the game application, wherein the plurality of virtual objects comprises one or more virtual color blindness indication objects categorized to a dichromatic visual deficiency type within the virtual environment, wherein the one or more virtual color blindness indication objects located at a designated location within the virtual environment, wherein each of the one or more virtual color blindness indication objects includes a set of colors that are visibly distinguishable within a categorized dichromatic visual spectrum;
render the plurality of virtual objects within the virtual environment including the one or more virtual color blindness indication objects;
prompt user interaction with the one or more virtual color blindness indication objects;
monitor the user interaction with the one or more virtual color blindness indication objects;
determine if the user interaction with the one or more virtual color blindness indication objects satisfies a dichromatic visual deficiency threshold; and
enable a dichromatic color blind accessibility setting based on the dichromatic visual deficiency threshold satisfied by the user interaction with the one or more virtual color blindness indication objects categorized to a dichromatic visual deficiency type, wherein the color blind accessibility setting adjusts the colors used for rendering frames during runtime of the game application.

12. The system of claim 11, wherein the categorized dichromatic visual type includes protanopia, deuteranopia, and tritanopia.

13. The system of claim 11, wherein the one or more virtual color blindness indication objects belong to a set.

14. The system of claim 11, wherein the colors of a virtual color blindness indication object form a perceivable pattern within a single dichromatic visual spectrum.

15. The system of claim 14, wherein arrival of a virtual entity controlled by the user at a designated virtual location within the virtual environment causes the prompting user interaction with the one or more virtual color blindness indication objects.

16. The system of claim 11, wherein the machine-readable instructions are further configured to categorize user interaction with virtual color blindness indication objects by visual deficiency type when monitoring user interaction.

17. The system of claim 11, wherein each dichromatic visual deficiency threshold requires a degree of user interaction with the one or more virtual color blindness indication objects categorized to the corresponding visual deficiency type.

18. The system of claim 11, wherein the machine-readable instructions are further configured to:
calculate a color generation ratio based on user interactions with virtual color blindness indication objects;
instantiate one or more virtual color blindness indication object sets based on the color generation ratio;
prompt the user to interact with the one or more virtual color blindness indication objects;
monitor user interaction with the one or more virtual color blindness indication objects;
determine if the user interaction with the one or more virtual color blindness indication objects satisfies an adjustment threshold; and
adjust the dichromatic visual deficiency setting in response to the user satisfying an adjustment threshold.

* * * * *